United States Patent
Suzuki

(10) Patent No.: US 9,173,844 B2
(45) Date of Patent: Nov. 3, 2015

(54) PHARMACEUTICAL SOLID PREPARATION

(75) Inventor: Kai Suzuki, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 13/062,389

(22) PCT Filed: Aug. 26, 2009

(86) PCT No.: PCT/JP2009/065283
§ 371 (c)(1),
(2), (4) Date: Mar. 4, 2011

(87) PCT Pub. No.: WO2010/026971
PCT Pub. Date: Mar. 11, 2010

(65) Prior Publication Data
US 2011/0165249 A1    Jul. 7, 2011

(30) Foreign Application Priority Data
Sep. 5, 2008 (JP) ................... 2008-228569

(51) Int. Cl.
*A61K 9/14*  (2006.01)
*A61K 9/20*  (2006.01)

(52) U.S. Cl.
CPC ............. *A61K 9/2018* (2013.01); *A61K 9/2027* (2013.01)

(58) Field of Classification Search
CPC ........................... A61K 9/2027; A61K 9/2018
See application file for complete search history.

(56) References Cited

U.S. PATENT DOCUMENTS

| | | | |
|---|---|---|---|
| 5,213,806 A | 5/1993 | Ito et al. | |
| 5,215,754 A | 6/1993 | Valorose et al. | |
| 2004/0219208 A1 * | 11/2004 | Kawamura et al. | 424/468 |
| 2004/0242659 A1 * | 12/2004 | Tasaka et al. | 514/374 |
| 2004/0247669 A1 * | 12/2004 | Gin et al. | 424/468 |

FOREIGN PATENT DOCUMENTS

| | | |
|---|---|---|
| EP | 0 273 209 A2 | 7/1988 |
| EP | 0 488 139 A1 | 6/1992 |
| JP | 05-502894 A | 5/1993 |
| JP | 7-126163 A | 5/1995 |
| JP | 11-509539 A | 8/1999 |
| WO | 92/03124 A1 | 3/1992 |
| WO | 97/03670 A1 | 2/1997 |
| WO | 2005/007105 A2 | 1/2005 |

OTHER PUBLICATIONS

Miyazaki et al, 2007, "Tolvaptan, an Orally Active Vasopressin V2-Receptor Antagonist—Pharmacology and Clinical Trials," Cardiovascular Drug Reviews vol. 25, No. 1, pp. 1-13.*
International Search Report of PCT/JP2009/065283 dated Dec. 10, 2009.

* cited by examiner

*Primary Examiner* — Suzanne Ziska
(74) *Attorney, Agent, or Firm* — Sughrue Mion, PLLC

(57) ABSTRACT

An object of the present invention is to provide a gradual disintegration-type, sustained-release pharmaceutical solid preparation whose pharmacologically active substance release behavior is controlled. The solid pharmaceutical preparation of the present invention is a matrix-type preparation containing: (a) a pharmacologically active substance; (b) calcium polycarbophil; and (c) a specific sugar and/or sugar alcohol.

18 Claims, 1 Drawing Sheet

PHARMACEUTICAL SOLID PREPARATION

CROSS REFERENCE TO RELATED APPLICATIONS

This application is a National Stage of International Application No. PCT/JP2009/065283 filed Aug. 26, 2009, claiming priority based on Japanese Patent Application No. 2008-228569, filed Sep. 5, 2008, the contents of all of which are incorporated herein by reference in their entirety.

TECHNICAL FIELD

The present invention relates to a pharmaceutical solid preparation.

BACKGROUND ART

There have been many attempts in the pharmaceutical industry to control drug release and maintain drug concentration in the blood at an appropriate level for a long period of time. In order to maintain drug concentration in the blood at an appropriate level for a long period of time, a pharmaceutical advancement (release control) to maintain drug absorption for a long time is necessary. Such release-controlled pharmaceutical preparations are referred to as "sustained-release preparations".

Sustained-release preparations are defined as pharmaceutical preparations in which the release rate, release time, and release location of the pharmaceutically active ingredient are controlled with the purpose of reducing the frequency of administration, or decreasing side effects. Immediate-release preparations are defined as pharmaceutical preparations whose pharmacologically active substance release is not particularly controlled. For example, with respect to oral preparations, water-insoluble matrix-type, hydrogel matrix-type, film coating-type, osmotic pump-type, or like sustained-release preparations are widely known.

Immediate-release preparations and sustained-release preparations can be classified according to the length of disintegration time of the pharmaceutical preparation, instead of whether the release is controlled or not. More specifically, immediate-release preparations disintegrate in a short time and immediately release a pharmacologically active substance. Sustained-release preparations disintegrate over a long period of time and gradually release a pharmacologically active substance. To control the disintegration rate of a pharmaceutical preparation, the incorporation of a disintegrant into the pharmaceutical preparation is important. To obtain a desired disintegration rate, the selection of an optimal disintegrant is also important. Disintegration induced by disintegrants can be roughly classified into two types: swelling and capillary action (wicking). Swelling-type disintegrants disintegrate pharmaceutical preparations with their excellent water absorption and swelling capabilities. In contrast, wicking-type disintegrants cause water to quickly penetrate into pores in the pharmaceutical preparation to break the bonds between particles, thus dispersing the particles.

However, each type of disintegrants, i.e., swelling-type disintegrants and wicking-type disintegrants, has disadvantages. Since even a small amount of swelling-type disintegrant is highly effective in quickly causing the internal disintegration of pharmaceutical preparations, disintegrants of this type are unsuitable for prolonged disintegration control, i.e., sustained release. Wicking-type disintegrants have a low swelling ability and are thus less likely to cause internal disintegration of pharmaceutical preparations. However, even a slight decrease or increase in the amount of wicking-type disintegrant may result in insufficient disintegration or disintegration behavior similar to that of immediate-release pharmaceutical preparations. That is, precise adjustment of the amount of wicking-type disintegrant is difficult.

It is thus extremely difficult to achieve sustained release by controlling disintegration through mere selection of a disintegrant and mere adjustment of the amount of disintegrant used.

SUMMARY OF INVENTION

Technical Problem

An object of the present invention is to provide a gradual disintegration-type, sustained-release pharmaceutical solid preparation whose pharmacologically active substance-release behavior is controlled.

Solution to Problem

To achieve the above object, the present inventor carried out extensive research. As a result, the inventor found that the desired sustained-release pharmaceutical solid preparation can be obtained by mixing specific components as described below. The present invention has been accomplished based on this finding.

The present invention provides pharmaceutical solid preparations described in Items 1 to 17.

Item 1. A matrix-type pharmaceutical solid preparation comprising: (a) a pharmacologically active substance; (b) calcium polycarbophil; and (c) a sugar and/or sugar alcohol, the (c) sugar and/or sugar alcohol being at least one member selected from the group consisting of trehalose, lactitol, maltose, maltitol, sucrose, sorbitol, xylitol, erythritol, mannitol, lactose, and isomaltooligosaccharide.

Item 2. The pharmaceutical solid preparation according to Item 1, wherein the amount of the (b) calcium polycarbophil is 1 to 50 wt. %.

Item 3. The pharmaceutical solid preparation according to Item 1, wherein the amount of the (c) sugar and/or sugar alcohol is 0.1 to 70 wt. %.

Item 4. The pharmaceutical solid preparation according to Item 1 further comprising (d) water-insoluble fine particles.

Item 5. The pharmaceutical solid preparation according to Item 4, wherein the (d) water-insoluble fine particles are particles that can reduce pores in the preparation.

Item 6. The pharmaceutical solid preparation according to Item 4, wherein the average particle diameter of the (d) water-insoluble fine particles is 0.002 to 50 μm.

Item 7. The pharmaceutical solid preparation according to Item 4, further comprising (e) a wicking-type disintegrant.

Item 8. The pharmaceutical solid preparation according to Item 7, wherein the (e) wicking-type disintegrant is carmellose.

Item 9. The pharmaceutical solid preparation according to Item 4, wherein the (d) water-insoluble fine particles are at least one member selected from the group consisting of colloidal silicon dioxide, hydrated silicon dioxide, light anhydrous silicic acid, talc, titanium oxide, magnesium stearate, and ethyl cellulose.

Item 10. The pharmaceutical solid preparation according to Item 9, wherein the average particle diameter of the (d) water-insoluble fine particles is 0.002 to 50 μm.

Item 11. The pharmaceutical solid preparation according to Item 4, wherein the amount of the (d) water-insoluble fine particles is 0.01 to 30 wt. %.

Item 12. The pharmaceutical solid preparation according to Item 7, wherein the amount of the (e) wicking-type disintegrant is 0.1 to 15 wt. %.

Item 13. The pharmaceutical solid preparation according to Item 1, wherein the (c) sugar and/or sugar alcohol is at least one member selected from the group consisting of trehalose, lactitol, maltose, maltitol, sucrose, sorbitol, xylitol, and isomaltooligosaccharide.

Item 14. The pharmaceutical solid preparation according to Item 1, wherein the (c) sugar and/or sugar alcohol is at least one member selected from the group consisting of maltose monohydrate, maltitol, lactitol monohydrate, and trehalose dihydrate.

Item 15. The pharmaceutical solid preparation according to Item 1, wherein the amount of the (a) pharmacologically active substance is 0.01 to 80 wt. %.

Item 16. The pharmaceutical solid preparation according to Item 1, wherein the (a) pharmacologically active substance is tolvaptan, cilostazol, or theophylline.

Item 17. The pharmaceutical solid preparation according to Item 16, wherein the (a) pharmacologically active substance is tolvaptan in the form of an amorphous powder obtained in the same manner as in Preparation Example 1.

Advantageous Effects of Invention

The pharmaceutical solid preparation of the present invention is a so-called gradual disintegration-type pharmaceutical solid preparation, which disintegrates while gradually releasing solid substance peeled off from the surface layer portion thereof. The preparation is a sustained-release pharmaceutical solid preparation that exhibits excellent constant dissolution behavior for a prolonged period of time.

The pharmaceutical solid preparation of the present invention exhibits similar pharmacologically active substance dissolution behavior whether the preparation is immersed in an acidic solution or in a neutral solution. More specifically, the pharmaceutical solid preparation of the present invention can release a pharmacologically active substance at a constant rate under various pH conditions, such as in the stomach, small intestine, large intestine, etc. without being influenced by the pH.

Since the disintegrated portion of the pharmaceutical solid preparation of the present invention is always limited to the surface layer portion thereof, the solid preparation of the present invention is less susceptible to the influence of meals.

DESCRIPTION OF EMBODIMENTS

Figure 1:
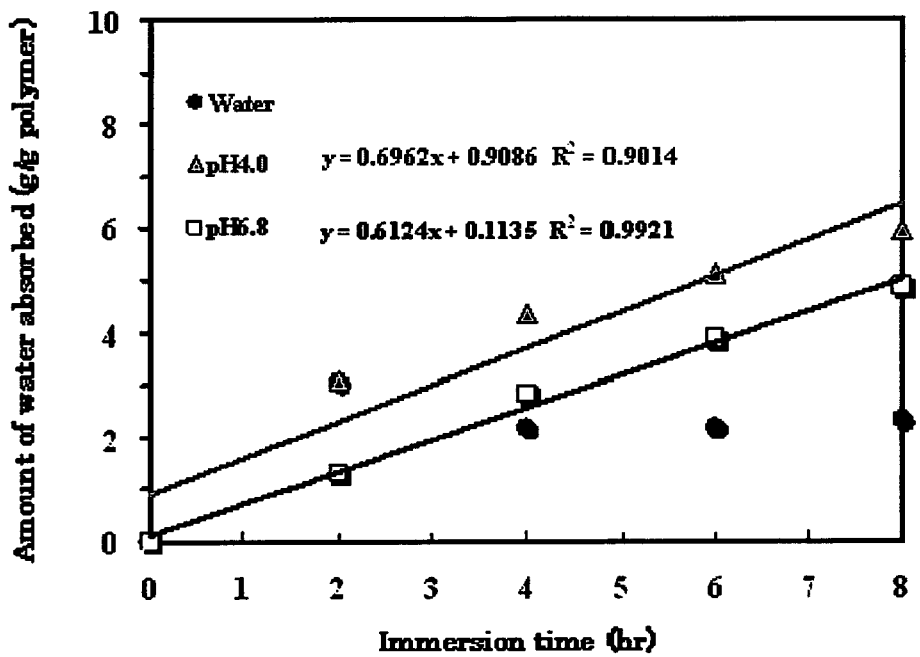
FIG. 1 is a graph showing the relationship between the immersion time and the amount of water absorbed by calcium polycarbophil in an acidic solution and in a neutral solution in Reference Example 1.

The pharmaceutical solid preparation of the present invention is a matrix-type preparation comprising (a) a pharmacologically active substance, (b) calcium polycarbophil, and (c) a sugar and/or sugar alcohol. The (c) sugar and/or sugar alcohol incorporated in the pharmaceutical solid preparation of the present invention is at least one member selected from the group consisting of trehalose, lactitol, maltose, maltitol, sucrose, sorbitol, xylitol, erythritol, mannitol, lactose, and isomaltooligosaccharide.

The pharmaceutical solid preparation of the present invention is a matrix-type preparation, and can be produced by uniformly mixing components (a) to (c). The pharmaceutical solid preparation of the present invention exhibits gradual disintegration behavior in a dissolution test. The gradual disintegration is such that disintegration does not occur in the entire pharmaceutical preparation; only a part of the pharmaceutical preparation, particularly the surface layer portion thereof, is disintegrated. This means that the penetration of water into the pharmaceutical preparation is precisely controlled.

(a) Pharmacologically Active Substance

The pharmacologically active substance used in the present invention is not particularly limited, insofar as it can be used as a pharmaceutically active ingredient to treat or prevent a disease. The pharmacologically active substance may be free compounds, salts thereof, solvates (hydrates, ethanolates, etc.) thereof, or crystal polymorphisms thereof. The pharmacologically active substance of the present invention is preferably a substance whose sustained release can suppress the expression of side effects, and increase therapeutic effects. The pharmacologically active substance may be crystalline or amorphous. The pharmacologically active substance may be water-soluble or lipid-soluble, or poorly soluble in water.

When the pharmacologically active substance is poorly soluble, a known pharmaceutical formulation technique such as nano-pulverization, pulverization, amorphization, crystallization, or nanocrystallization can be used to improve the solubility of the poorly soluble pharmacologically active substance. For example, as shown in Preparation Example 1, a pharmacologically active substance is dissolved singly, or in combination with hydroxypropylcellulose (HPC) or like water-soluble polymers, in an appropriate solvent (such as ethanol, dichloromethane, etc.), and the resulting solution is spray dried to form an amorphous powder. Alternatively, as shown in Preparation Example 2, a pharmacologically active substance and sodium lauryl sulfate (SLS) are mixed and pulverized with a mill, such as a jet mill, to form a finely pulverized product.

Examples of pharmacologically active substances that can be used in the present invention include 5-aminosalicylic acid, acyclovir, aspirin, acetylsalicylic acid, acetaminophen, aripiprazole, ampicillin, isoniazid, ibuprofen, indomethacin, escitalopram, ethenzamide, enalapril, erythromycin, omeprazole, glimepiride, ketoconazole, conivaptan, satavaptan, salbutamol, salazosulfapyridine, salazopyrin, diazepam, diclofenac, diclofenac sodium, dipyridamole, cimetidine, cilostazol, simvastatin, sucralfate, sulpiride, sulfasalazine, celecoxib, tacrolimus, theophylline, tegafur, dexamethasone, dextromethorphan, tetomilast, terfenadine, doxorubicin, triamcinolone, tolvaptan, nadifloxacin, naproxen, nifedipine, urea, sodium valproate, haloperidol, valacyclovir, paliperidone, hydrocortisone, pioglitazone, famotidine, phenacetin, phenytoin, phenylpropanolamine, budesonide, pravastatin, pravastatin sodium, fluorouracil, prednisolone, prednisone, furosemide, probucol, vesnarinone, penicillin, perphenazine, voglibose, chlorpheniramine maleate, midazolam, doxazosin mesilate, methotrexate, morphine, ranitidine, lansoprazole, lisinopril, risperidone, lidocaine, rivoglitazone, rebamipide, levodopa, rotigotine, lovastatin, lorazepam, warfarin, ambroxol hydrochloride, carteolol hydrochloride, diphenhydramine hydrochloride, tamsulosin hydrochloride, nicardipine hydrochloride, hydralazine hydrochloride, pioglitazone hydrochloride, buprenorphine hydrochloride, procaterol hydrochloride, mozavaptane hydrochloride, ranitidine hydrochloride, levocarnitine hydrochloride, cortisone acetate, salbutamol sulfate, and the like. Among these, cilostazol, tolvaptan, rebamipide, procaterol hydrochloride, aripiprazole, and theophylline are preferable, and tolvaptan, cilostazol, and theophylline are most preferable.

The amount of pharmacologically active substance in the pharmaceutical preparation is typically 0.01 to 80 wt. %, preferably 0.1 to 70 wt. %, and more preferably 1 to 50 wt. %.

(b) Calcium Polycarbophil

Calcium polycarbophil that is of a quality suitable for pharmaceutical use is preferably used. More specifically, a wide variety of known compounds that conform to United States Pharmacopeia (USP31) can be used as the calcium polycarbophil. Calcium polycarbophil is a calcium salt of an acrylic acid polymer cross-linked with divinyl alcohol.

Preferably, the calcium polycarbophil has a calcium content of 18 to 22 wt. %, and a water-absorbing power is not less than 35.0 g-sodium bicarbonate aqueous solution/g-dry calcium polycarbophil, i.e., the amount of sodium bicarbonate aqueous solution absorbed per 1 g of calcium polycarbophil that calculated on the dried basis is not less than 35.0 g, as determined by the method according to United States Pharmacopeia (USP31). From the viewpoint of appropriate mixing with other components, calcium polycarbophil preferably has a particle size distribution such that particles with a size of less than 75 μm account for 10% or more of calcium polycarbophil, and particles with a size of 250 μm or more account for 10% or less, as determined by, for example, using a fully automatic sonic vibrating screen classifier ("Robot Shifter RPS-95" manufactured by Seishin Enterprise Co., Ltd.). Examples of commercially available calcium polycarbophil products include "Noveon CA-1" and "Noveon CA-2" manufactured by Lubrizol Corp., "Carbopol EX-83 Resin" and "Carbopol EX-788 Resin" manufactured by B.F. Goodrich Company, "Calcium Polycarbophil" manufactured by Boehringer Ingelheim Chemicals, Inc., and the like.

When preparing a pharmaceutical solid preparation of the present invention, the obtained pharmaceutical solid preparation may contain, in addition to calcium polycarbophil, a small amount of polycarbophil that is produced by the removal of calcium from calcium polycarbophil that may occur in any one of the steps in the production process.

The amount of calcium polycarbophil in the pharmaceutical solid preparation is typically 1 to 50 wt. %, preferably 7 to 40 wt. %, and more preferably 10 to 30 wt. %.

(c) Sugar and/or Sugar Alcohol

The (c) sugar and/or sugar alcohol that is used in the present invention may be at least one member selected from the group consisting of trehalose, lactitol, maltose, maltitol, sucrose, sorbitol, xylitol, erythritol, mannitol, lactose, and isomaltooligosaccharide. Among these, trehalose, lactitol, maltose, maltitol, sucrose, sorbitol, xylitol, and isomaltooligosaccharide are preferable.

The sugar and/or sugar alcohol that are used in the present invention may be in the form of a hydrate.

In the present invention, it is particularly preferable to use the sugars and/or sugar alcohols described below; the commercially available products shown below can also be used.

Trehalose dihydrate (for example, "Trehalose P" manufactured by Asahi Kasei Chemicals Corporation, and "Treha" manufactured by Hayashibara Co., Ltd.);

Lactitol monohydrate (for example, "Lactitol LC-1" manufactured by Nikkne Chemical and Synthetic Industry Co., Ltd.);

Maltose monohydrate (for example, "Sunmalt-S" manufactured by Sanwa Cornstarch Co., Ltd., and "Nisshoku Crystalline Maltose" manufactured by Nihon Shokuhin Kako Co., Ltd.);

Maltitol (for example, the "Maltisorb" series manufactured by Roquette; and "habit" manufactured by Hayashibara Biochemical Laboratories, Inc.);

Sucrose (for example, "Granulated sugar CH" manufactured by Ensuiko Sugar Refining Co., Ltd.);

Sorbitol (for example, "Sorbitol SP" manufactured by Nikkne Chemical and Synthetic Industry Co., Ltd., "Neosorb powder" manufactured by Roquette, and "Sorbit DP-10M" manufactured by Towa-Kasei Co, Ltd.);

Xylitol (for example, "Xylitol P" manufactured by Nikkne Chemical and Synthetic Industry Co., Ltd., "Xylisorb" manufactured by Roquette, and "Xylit P" manufactured by Towa Chemical Industries Co, Ltd.; etc.

Examples of the most preferable sugars and/or sugar alcohols include maltose monohydrate, maltitol, lactitol monohydrate, and trehalose dihydrate. Such sugars and/or sugar alcohols can be used singly or in a combination of two or more.

The amount of sugar and/or sugar alcohol in the pharmaceutical solid preparation is typically 0.1 to 70 wt. %, preferably 1 to 60 wt. %, and more preferably 5 to 50 wt. %.

The pharmaceutical solid preparation of the present invention may further contain (d) water-insoluble fine particles and/or (e) a capillary action-type (wicking-type) disintegrant, in addition to the above components (a) to (c).

(d) Water-Insoluble Fine Particles

Examples of the (d) water-insoluble fine particles used in the present invention include known water-insoluble fine particles that can reduce pores in a pharmaceutical solid preparation. Penetration of water into the pharmaceutical solid preparation can be precisely controlled by filling the pores inside of the pharmaceutical solid preparation with such water-insoluble fine particles. When the pharmaceutical solid preparation of the present invention further contains the (d) water-insoluble fine particles, the preparation can release a pharmacologically active substance at a constant speed, particularly when it is in an acidic solution or in a neutral solution, and the preparation can exhibit excellent sustained-release performance under various pH conditions; for example, in the stomach, intestines, etc.

The average particle diameter of the (d) water-insoluble fine particles is typically 0.002 to 50 μm, preferably 0.005 to 40 μm, and more preferably 0.01 to 30 μm. The average particle diameter of the (d) water-insoluble fine particles can be determined by the laser diffraction method or by direct measurement through electron microscopic observation.

Since the (d) water-insoluble fine particles do not dissolve in water that penetrates into the pharmaceutical preparation, no pores are newly formed, and the permeability of water into the pharmaceutical preparation can be retained.

Examples of water-insoluble fine particles include inorganic compounds such as colloidal silicon dioxide, hydrated silicon dioxide, light anhydrous silicic acid, talc, and titanium oxide; fatty acid metal salt compounds such as magnesium stearate, and calcium stearate; water-insoluble polymer compounds such as ethyl cellulose and amino alkyl methacrylate copolymer RS; and the like. Examples of preferable water-insoluble fine particles include colloidal silicon dioxide, hydrated silicon dioxide, light anhydrous silicic acid, talc, titanium oxide, magnesium stearate, ethyl cellulose, and the like. Such water-insoluble fine particles can be used singly or in a combination of two or more.

When two kinds of water-insoluble fine particles are used in combination, the combined use of a water-insoluble polymer compound with an inorganic compound and/or a fatty acid metal salt compound can dilute the concentration of the pharmacologically active substance while the preparation maintains its pharmacologically active ingredient substance release-controlling effect. Accordingly, the release-controlling effect of the present invention can be produced even when using a low-dose pharmacologically active substance, such as a compound with potent pharmacological activity. Examples of preferable combinations are combinations of ethyl cellulose as a water-insoluble polymer compound with an inorganic compound, such as colloidal silicon dioxide, hydrated silicon dioxide, light anhydrous silicic acid, talc, or titanium oxide, or with a fatty acid metal salt, such as magnesium stearate or calcium stearate.

Examples of more preferable combinations include combinations of ethyl cellulose with at least one member selected from the group consisting of colloidal silicon dioxide, hydrated silicon dioxide, light anhydrous silicic acid, talc, titanium oxide, and magnesium stearate.

When two kinds of water-insoluble particles are used in combination, the mixing weight ratio of the water-insoluble polymer to the inorganic compound and/or to the fatty acid metal salt is typically in the range of 4:1 to 1:4, and preferably 3:1 to 1:1.

When three or more kinds of water-insoluble fine particles are used in combination, at least one kind of water-insoluble polymer compound and at least two kinds of inorganic compounds and/or fatty acid metal salt compounds are used in combination.

The amount of the (d) water-insoluble fine particles in the pharmaceutical solid preparation is typically 0.01 to 30 wt. %, preferably 0.1 to 20 wt. %, and more preferably 0.5 to 15 wt. %, from the viewpoint of appropriate mixing, appropriate fluidity, compression moldability, etc.

Preferable water-insoluble fine particles are described below in more detail. The preferable water-insoluble fine particles are of a quality usable in the medicinal field and are easily available.

(d-i) Colloidal Silicon Dioxide:

Colloidal silicon dioxide is a submicroscopic silica having a primary particle diameter of about 15 nm. Colloidal silicon dioxide is a blue-white tasteless odorless amorphous powder (as described on page 250 of "Handbook of Pharmaceutical Excipients", editorial supervisor Tsuneji Nagai, translated and edited by Japan Pharmaceutical Excipients Council, publisher Yakuji Nippo Limited, 2001). Colloidal silicon dioxide is produced by high temperature hydrolysis of a chlorosilane, such as silicon tetrachloride, in an oxygen hydrogen flame (as described in a product brochure of Nippon Aerosil Co., Ltd.). Examples of colloidal silicon dioxide that can be used in the present invention include commercially available products, such as "Aerosol 200" manufactured by Nippon Aerosil Co., Ltd.

(d-ii) Hydrated Silicon Dioxide:

Sodium silicate produced using a high-purity silica sand as a starting material is mixed with sulfuric acid to produce a silicic acid sol. The silicic acid sol is polymerized to produce primary particles, which are converted to three-dimensional secondary aggregates. In this process, hydrated silicon dioxide is produced by controlling the aggregate growth. This process is called "the wet method", which is distinguished from the method of producing colloidal silicon dioxide, light anhydrous silicic acid ("the dry method") (as described in a product brochure of Fuji Silysia Chemical Ltd.). Hydrated silicon dioxide has an average particle diameter of about 5 μm. Examples of hydrated silicon dioxide that can be used in the present invention include commercially available products. For example, "Adsolider-102" manufactured by Fuji Silysia Chemical Ltd. can be used.

(d-iii) Light Anhydrous Silicic Acid:

Light anhydrous silicic acid can be produced by a method similar to the method of producing hydrated silicon dioxide; however, gelation is allowed to proceed without particularly controlling the aggregate growth, and the obtained gel is dried and then pulverized into a micron-sized powder (as described in a product brochure of Fuji Silysia Chemical Ltd.). Light anhydrous silicic acid has an average particle diameter of 2 to 4 μm. Examples of light anhydrous silicic acids that can be used in the present invention include commercially available products. For example, "Adsolider-101" manufactured by YKF Inc. can be used.

(d-iv) Talc:

Talc is a hydrous polysilicate mineral that is present in nature. Talc mainly consists of a purified hydrous magnesium silicate with the chemical formula $Mg_6(Si_2O_5)_4(OH)_4$, and may contain a small amount of aluminium silicate and iron. Talc is produced in the following manner. After mining, asbestos, carbon, dolomite, iron oxide, and all the other magnesium and carbonate minerals are removed by the flotation method, and then pulverized. Subsequently, the obtained powder is treated with dilute hydrochloric acid, washed with water, and then dried (as described on pages 404 to 405 of "Handbook of Pharmaceutical Excipients", editorial supervisor Tsuneji Nagai, translated and edited by Japan Pharmaceutical Excipients Council, publisher Yakuji Nippo Ltd., 2001). Examples of the talc that can be used in the present invention include commercially available products. For example, "MMR" (average particle diameter: about 4 μm) manufactured by Asada Milling Co., Ltd., and "PKP-81" (average particle diameter: about 14 μm) manufactured by Fuji Talc Industrial Co., Ltd. can be used.

(d-v) Titanium Oxide:

Titanium oxide is an amorphous, tasteless, odorless, non-hygroscopic powder. The titanium oxide powder has an average particle size of 1 μm or less. Titanium oxide may exist in various crystalline forms, such as rutile, anatase, and brookite. The forms that are important in the medicinal field are rutile and anatase; and rutile is more thermally stable and dominant. Titanium oxide is produced by direct bonding of titanium to oxygen, treatment of a titanium salt in an aqueous solution, reaction of a volatile inorganic titanium compound with oxygen, and oxidation or hydrolysis of an organic titanium compound (as described on pages 279 to 281 of "Handbook of Pharmaceutical Excipients", editorial supervisor Tsuneji Nagai, translated and edited by Japan Pharmaceutical Excipients Council, publisher Yakuji Nippo Ltd., 2001). Examples of the titanium oxide that can be used in the present invention include commercially available products. For example, "A-HR" manufactured by Freund Industrial Co., Ltd. and "Tipaque A-100" manufactured by Ishihara Sangyo Kaisha, Ltd. can be used.

(d-vi) Magnesium Stearate:

Magnesium stearate is a very fine, white, precipitated or milled, amorphous, bulky, hydrophobic powder. The average particle diameter of magnesium stearate is 4 to 12 μm. Magnesium stearate may exist in various crystalline forms. Magnesium stearate for industrial use is a mixture of crystalline structures (as described on pages 343 to 345 of "Handbook of Pharmaceutical Excipients", editorial supervisor Tsuneji Nagai, translated and edited by Japan Pharmaceutical Excipients Council, publisher Yakuji Nippo Ltd., 2001). The precipitation method and the fusion method are known as methods for producing magnesium stearate. The precipitation method has been widely used, because a uniform-quality light magnesium stearate can be easily produced thereby. First, stearic acid and sodium hydroxide are heated and allowed to react. Subsequently, an aqueous solution of magnesium sulfate is added to yield a precipitate of magnesium stearate. The precipitate is filtered, washed with water, dried, and pulverized into a fine powder to obtain a final product (as described on pages 76 to 77 of "Iyakuhin Tenkabutsu Yoran" (Handbook of Pharmaceutical Additives), editorial supervisor Yoshihisa Matsuda, publisher Jiho Inc., 1992). In recent years, vegetable-derived stearic acid has been used as a starting material. Examples of magnesium stearate that can be used in the present invention include commercially available products. For example, "vegetable magnesium stearate" manufactured by Taihei Chemical Industrial Co., Ltd. can be used.

(d-vii) Ethyl Cellulose

Ethyl cellulose is a water-insoluble thermoplastic cellulose ether widely used for oral pharmaceutical preparations. Ethyl cellulose having an ethoxyl content of 46.5 to 51 wt. % is allowed to be used for pharmaceutical purposes in Japan, the U.S., and Europe. There are various grades and various viscosities of ethyl cellulose, which are classified according to the ethoxyl content and the viscosity. For example, "Ethocel", which is ethyl cellulose manufactured by The Dow Chemical Company, includes the "Ethocel MED" series with an ethoxyl content of 45.0 to 47.0 wt. %, the "Ethocel STD" series with an ethoxyl content of 48.0 to 49.5 wt. %, and the "Ethocel HE" series with an ethoxyl content of 49.6 to 53.0 wt. %. Each series has viscosity variations, which range from 4 to 200 cps. For pharmaceutical use, "Ethocel Premium" of the Ethocel STD series is particularly preferable. Further, "Aqualon Ethylcellulose", which is ethyl cellulose manufactured by Hercules Inc., includes the "Aqualon K" series with an ethoxyl content of 45.0 to 47.2 wt. %, the "Aqualon N" series with an ethoxyl content of 48.0 to 49.5 wt. %, and the "Aqualon T" series with an ethoxyl content of 49.6 to 51.5 wt. %. Each series has viscosity variations, which range from 4 to 300 cps. In particular, "Aqualon T10 Pharm EC" of the Aqualon T series is suitable for pharmaceutical use (as described in the technological data in "Aqualon Ethylcellulose" products of Hercules Inc.).

The Dow Chemical Company's "Ethocel STD" series has a variation in powder grade, and includes "Ethocel 7FP" with a viscosity of 3.5 to 5.5 cps, "Ethocel 10FP" with a viscosity of 9.0 to 11.0, and "Ethocel 100FP" with a viscosity of 90.0 to 110.0 cps. "Ethocel 7FP" has an average particle diameter of 5 to 15 μm, "Ethocel 10FP" has an average particle diameter of 3 to 15 μm, and "Ethocel 100FP" has an average particle diameter of 30 to 60 μm (as described in the technological data of "Ethocel" products of Nisshin Kasei Co., Ltd.).

Examples of the ethyl cellulose that can be used in the present invention include commercially available products. For example, "Ethocel Premium STD-7FP" and "Ethocel Premium STD-10FP" manufactured by The Dow Chemical Company can be used. These ethyl celluloses have an average particle diameter of 5 to 15 μm.

(e) Capillary-Action Type (Wicking-Type) Disintegrant

As used herein, the wicking-type disintegrant refers to a disintegrant which itself functions as a so-called conduit to penetrate water into pharmaceutical preparations.

Examples of the (e) wicking-type disintegrant include carmellose. The disintegration rate of a pharmaceutical solid preparation can be appropriately controlled by incorporating a wicking-type disintegrant into the preparation, whereby the release rate of a pharmacologically active substance can be more effectively controlled. For example, a higher release rate of a pharmacologically active substance can be achieved by increasing the proportion of the wicking-type disintegrant in the pharmaceutical preparation. A lower release rate of a pharmacologically active substance can be achieved by decreasing the proportion of the wicking-type disintegrant in the preparation.

A wicking-type disintegrant causes water to quickly penetrate into a pharmaceutical preparation. To control penetration of water into a pharmaceutical preparation and disintegrate only the surface layer portion of the pharmaceutical preparation as in the present invention, it is more effective to use a wicking-type disintegrant in combination with the (d) water-insoluble fine particles.

The amount of the (e) wicking-type disintegrant in the pharmaceutical solid preparation is typically 0.1 to 15 wt. %, preferably 0.5 to 10 wt. %, and more preferably 1 to 7.5 wt. %.

Carmellose that is of a quality usable in the pharmaceutical field and that is easily available is used as carmellose in the present invention. Carmellose is an acidic cellulose derivative chemically modified with carboxymethyl, and can be produced by reducing the pH of carmellose sodium with a mineral acid to precipitate carmellose. Although carmellose belongs to acidic carboxylic acids, carmellose is very slightly acidic, and has a dissociation constant of $1.4 \times 10^{-3}$ and a buffering effect. Compared to other general disintegration adjuvants and disintegrants, carmellose has low water absorption and poor swelling capabilities. However, carmellose has excellent water wettability, and thereby causes water to quickly penetrate into a pharmaceutical preparation to break the bonds between particles in the pharmaceutical preparation, thus promoting disintegration (as described in the technical data on carmellose of Gotoku Chemical Co., Ltd.). Examples of the carmellose that can be used in the present invention include commercially available products. For example, "NS-300" manufactured by Nichirin Chemical Industries, Ltd. can be used.

The pharmaceutical solid preparation of the present invention may further contain other components in addition to the above components (a) to (c), and component (d) and/or component (e). Examples of such other components include diluents, binders, pH adjusters, absorption promoters, lubricants, coloring agents, taste-masking agents, flavors, coatings, and like various additives that can be incorporated into solid pharmaceutical preparations. If necessary, the pharmaceutical solid preparation may be film-coated. These components can be incorporated into the pharmaceutical solid preparation of the present invention, insofar as they do not impair the effect of the present invention.

The pharmaceutical solid preparation of the present invention can be produced by mixing the above-mentioned components and performing a known method. For example, a direct tableting method may be used, or a dry granulation method, a wet granulation method, or like methods may be used to produce granules, which are then subjected to a tableting method to produce a pharmaceutical solid preparation. A specific example of a process of producing the solid preparation of the present invention in the form of a tablet comprises a mixing step and a tableting step, and may optionally comprise, before or after these steps, a dry granulation step, a wet granulation step, a drying step, a particle size-regulating step, etc. After the tableting step, a film-coating step may be performed. The pharmaceutical solid preparation of the present invention can be produced by using a manufacturing apparatus that is generally and widely used in the pharmaceutical field.

The dosage form of the pharmaceutical solid preparation is not particularly limited, and may be, for example, tablets, granules, capsules, etc. When the preparation is in the form of a capsule, the capsule may contain one or more kinds of tablets and/or granules therein. From the viewpoint of ease of handling and ease of administration, the dosage form of the pharmaceutical solid preparation of the present invention is preferably tablets or capsules.

When the pharmacologically active substance contained in the pharmaceutical solid preparation of the present invention is unstable in light or has an unpleasant taste or odor, a coating film generally used may be formed on the tablet to mask the substance, thus improving the quality and facilitating the administration. Further, from the viewpoint of improving the tablet strength and preventing problems relating to humidity, a coating film may be formed, insofar as it does not impair the effect of the present invention.

When the pharmaceutical solid preparation of the present invention is formed into a tablet, the tablet preferably has a diameter or length of 3 to 30 mm from the viewpoint of productivity, ease of handling, and ease of administration. When the pharmaceutical solid preparation of the present invention is formed into a granule, the granule preferably has a particle diameter of 0.3 to 3 mm from the viewpoint of productivity. When the pharmaceutical solid preparation of the present invention is formed into a capsule, the capsule size is preferably No. 5 to No. 00 from the viewpoint of ease of handling and ease of administration.

EXAMPLES

The present invention will be explained in more detail with reference to Reference Examples, Examples, and Comparative Examples.

Reference Example 1

Water Absorption Test on Water-Absorbing Polymers (1.1) Water-Absorbing Polymers The following five types of water-absorbing polymers were tested for their water-absorbing abilities:
(a) calcium polycarbophil, trade name "Noveon CA-1", manufactured by The Lubrizol Corporation (this water-absorbing polymer is hereinafter referred to as "CA-1");
(b) polyvinyl alcohol, trade name "Gohsenol AH-17", manufactured by Nippon Synthetic Chemical Industries, Ltd. (this water-absorbing polymer is hereinafter referred to as "AH-17");
(c) a carboxyvinyl polymer, trade name "Carbopol 71GNF", manufactured by The Lubrizol Corporation (this water-absorbing polymer is hereinafter referred to as "71GNF");
(d) cross-linked and branched sodium polyacrylate, trade name "Junlon PW-110", manufactured by Nihon Junyaku Co., Ltd." (this water-absorbing polymer is hereinafter referred to as "PW-110"); and
(e) polycarbophil, trade name "Noveon AA-1", manufactured by The Lubrizol Corporation (this water-absorbing polymer is hereinafter referred to as "AA-1").

(1.2) Test Method: the Tea Bag Method (Evaluation of Water-Absorbing Capability)

About 0.5 g of a dry water-absorbing polymer with a particle diameter in the range of 106 to 300 μm was placed into each tea bag (70 mm×95 mm) made of a non-woven polyester fabric. The polymer-containing tea bags thus prepared were immersed in an excess amount of Test liquid A or in an excess amount of Test liquid B to allow the polymer to absorb water at 20±5° C. for 2, 4, 6, and 8 hours, after which the tea bags were taken out of the liquid to drain the water for 1 minute, and the weight (g) of each tea bag was then measured. The value thus obtained is defined as (x). The same procedure as above was repeated using the tea bag alone, and the weight (g) of the tea bag was measured, as a control, with time. The value thus obtained is defined as (y). The amount of water absorbed (g per 1 g of the polymer) was calculated by subtracting (y) from (x) and dividing this value by the dry weight of the water-absorbing powder as in the following equation:

Amount of water absorbed=$\{(x)-(y)\}$/(Dry weight of the water-absorbing polymer).

Table 1 shows the results obtained by immersing tea bags in Test liquid A. Table 2 shows the results obtained by immersing tea bags in Test liquid B. The following liquids were used as Test liquids A and B.

Test liquid A: diluted McIlvaine buffer (acidic solution), pH 4.0.

Test liquid B: The Second fluid for the dissolution test in Japanese Pharmacopoeia (neutral solution), pH 6.8.

TABLE 1

| Immersion time in Test liquid A | Amount of water absorbed by water-absorbing polymer (g per 1 g of the polymer) | | | | |
|---|---|---|---|---|---|
| | CA-1 | AH-17 | 71GNF | PW-110 | AA-1 |
| 2 | 3.1 | 5.6 | 9.8 | 15.4 | 28.6 |
| 4 | 4.3 | 6.4 | 13.7 | 20.7 | 33.5 |
| 6 | 5.1 | 6.3 | 15.8 | 24.7 | 35.2 |
| 8 | 6.0 | 7.3 | 18.6 | 27.4 | 37.9 |

TABLE 2

| Immersion time in Test liquid B | Amount of water absorbed by water-absorbing polymer (g per 1 g of the polymer) | | | | |
|---|---|---|---|---|---|
| | CA-1 | AH-17 | 71GNF | PW-110 | AA-1 |
| 2 | 1.3 | 3.7 | 10.9 | 13.9 | 26.7 |
| 4 | 2.8 | 4.9 | 18.1 | 23.4 | 34.7 |
| 6 | 3.9 | 6.5 | 21.4 | 27.1 | 37.2 |
| 8 | 4.8 | 6.6 | 25.8 | 33.4 | 39.3 |

(1.3) Test Results and Examination

The amount of water absorbed by calcium polycarbophil "CA-1" increased with time, when CA-1 was immersed in a test solution of pH 4.0 or in a test solution of pH 6.8. However, the amount of water absorbed by CA-1 was small, compared to other water-absorbing polymers (AH-17, 71GNF, and PW-110).

The amount of water absorbed by calcium polycarbophil was plotted versus the time. FIG. 1 shows the results.

As shown in FIG. 1, the test results clearly show that calcium polycarbophil absorbs water at a substantially constant rate, whether the test solution has a pH of 4.0 or 6.8. Since a correlation coefficient of $R^2 \geq 0.9$ was obtained, a good correlation was confirmed.

Preparation Example 1

Production Process of Amorphous Powder Tolvaptan

Amorphous tolvaptan was prepared in the following manner. One hundred grams of tolvaptan (7-chloro-5-hydroxy-1-[2-methyl-4-(2-methylbenzoylamino)benzoyl]-2,3,4,5-tetrahydro-1H-benzoazepine) and 50 g of hydroxypropylcellulose (HPC-SL, manufactured by Nippon Soda Co., Ltd., hydroxypropoxyl content: 53-78 weight %)

were dissolved in a mixed solvent of 1,390 g of dichloromethane and 350 g of ethanol. The resulting mixture was treated by a spray dryer (ODT-8 model; manufactured by Ohkawara Kakohki Co., Ltd.), and immediately dried by a vacuum dryer (LCV-232, manufactured by Tabai Espec Corp.), obtaining amorphous powder (amorphous tolvaptan).

The tolvaptan amorphous powders used in the following Examples and Comparative Examples were prepared in the same manner as in Preparation Example 1.

Preparation Example 2

Production Process of a Finely Pulverized Mixture of Cilostazol and SLS

Cilostazol (manufactured by Otsuka Pharmaceutical Co. Ltd., 100 g) and 5 g of sodium lauryl sulfate (SLS, manufactured by Nikko Chemicals Co., Ltd.) were mixed, and then finely cogrinded using a jet mill (100AS model, manufactured by Powrex Corporation).

Example 1

9 g of powder amorphous tolvaptan that had been made amorphous together with hydroxypropylcellulose, 2.9 g of maltitol (Maltisorb P90, manufactured by Roquette), 3 g of calcium polycarbophil (Noveon CA-1, manufactured by Lubrizol Corporation), and 0.1 g of magnesium stearate (plant origin, manufactured by Taihei Chemical Industrial Co., Ltd., average particle diameter: 6 μm) were well mixed. The resulting mixture was formed into round tablets having a weight of about 150 mg and a diameter of 7.5 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 2

9 g of powder amorphous tolvaptan that had been made amorphous together with hydroxypropylcellulose, 2.6 g of maltitol (Maltisorb P90, manufactured by Roquette), 3 g of calcium polycarbophil (Noveon CA-1, manufactured by Lubrizol Corporation), 0.3 g of colloidal silicon dioxide (Aerosil 200, manufactured by Aerosil Co., Ltd., average particle diameter: 0.015 μm) and 0.1 g of magnesium stearate (plant origin, manufactured by Taihei Chemicals Limited, average particle diameter: 6 μm) were well mixed. The resulting mixture was formed into round tablets having a weight of about 150 mg and a diameter of 7.5 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 3

9 g of powder amorphous tolvaptan that had been made amorphous together with hydroxypropylcellulose, 4.4 g of maltose monohydrate (Sunmalt-S, manufactured by Sanwa Cornstarch Co., Ltd.), 3.6 g of calcium polycarbophil (Noveon CA-1, manufactured by Lubrizol Corporation), 0.9 g of carmellose (NS-300, manufactured by Nichirin Chemical Industries, Ltd.) and 0.1 g of magnesium stearate (plant origin, manufactured by Taihei Chemicals Limited, average particle diameter: 6 μm) were well mixed. The resulting mixture was formed into round tablets having a weight of about 180 mg and a diameter of 8 mm, and containing 60 mg of active ingredient; the tablets were prepared using a universal testing instrument (Autograph AG-I model, manufactured by Shimadzu Corporation) under a compressive force of 10 kN and compression speed of 50 mm/min.

Example 4

9 g of powder amorphous tolvaptan that had been made amorphous together with hydroxypropylcellulose, 7.4 g of maltitol (Maltisorb P90, manufactured by Roquette), 0.2 g of calcium polycarbophil (Noveon CA-1, manufactured by Lubrizol Corporation), 0.9 g of carmellose (NS-300, manufactured by Nichirin Chemical Industries, Ltd.), 0.4 g of colloidal silicon dioxide (Aerosil 200, manufactured by Aerosil Co., Ltd., average particle diameter: 0.015 μm) and 0.2 g of magnesium stearate (plant origin, manufactured by Taihei Chemicals Limited, average particle diameter: 6 μm) were well mixed. The resulting mixture was formed into round tablets having a weight of about 180 mg and a diameter of 7.5 mm, and containing 60 mg of active ingredient; the tablets were prepared using a universal testing instrument (Autograph AG-I model, manufactured by Shimadzu Corporation) under a compressive force of 7 kN and compression speed of 100 mm/min.

Example 5

9 g of powder amorphous tolvaptan that had been made amorphous together with hydroxypropylcellulose, 6.6 g of maltitol (Maltisorb P90, manufactured by Roquette), 0.9 g of calcium polycarbophil (Noveon CA-1, manufactured by Lubrizol Corporation), 0.9 g of carmellose (NS-300, manufactured by Nichirin Chemical Industries, Ltd.), 0.4 g of colloidal silicon dioxide (Aerosil 200, manufactured by Aerosil Co., Ltd., average particle diameter: 0.015 μm) and 0.2 g of magnesium stearate (plant origin, manufactured by Taihei Chemicals Limited, average particle diameter: 6 μm) were well mixed. The resulting mixture was formed into round tablets having a weight of about 180 mg and a diameter of 7.5 mm, and containing 60 mg of active ingredient; the tablets were prepared using a universal testing instrument (Autograph AG-I model, manufactured by Shimadzu Corporation) under a compressive force of 7 kN and compression speed of 100 mm/min.

Example 6

9 g of powder amorphous tolvaptan that had been made amorphous together with hydroxypropylcellulose, 5.7 g of maltitol (Maltisorb P90, manufactured by Roquette), 7.2 g of calcium polycarbophil (Noveon CA-1, manufactured by Lubrizol Corporation), 1.8 g of carmellose (NS-300, manufactured by Nichirin Chemical Industries, Ltd.), 0.2 g of colloidal silicon dioxide (Aerosil 200, manufactured by Aerosil Co., Ltd., average particle diameter: 0.015 μm) and 0.2 g of magnesium stearate (plant origin, manufactured by Taihei Chemicals Limited, average particle diameter: 6 μm) were well mixed. The resulting mixture was formed into round tablets having a weight of about 240 mg and a diameter of 8.5 mm, and containing 60 mg of active ingredient; the tablets were prepared using a universal testing instrument (Autograph AG-I model, manufactured by Shimadzu Corporation) under a compressive force of 9 kN and compression speed of 50 mm/min.

Example 7

9 g of powder amorphous tolvaptan that had been made amorphous together with hydroxypropylcellulose, 11.7 g of maltose monohydrate (Sunmalt-S, Sanwa Cornstarch Co., Ltd.), 2.4 g of calcium polycarbophil (Noveon CA-1, manufactured by Lubrizol Corporation), 0.6 g of carmellose (NS-300, manufactured by Nichirin Chemical Industries, Ltd.), 0.1 g of colloidal silicon dioxide (Aerosil 200, manufactured by Aerosil Co., Ltd., average particle diameter: 0.015 µm) and 0.2 g of magnesium stearate (plant origin, manufactured by Taihei Chemicals Limited, average particle diameter: 6 µm) were well mixed. The resulting mixture was formed into round tablets having a weight of about 240 mg and a diameter of 8.5 mm, and containing 60 mg of active ingredient; the tablets were prepared using a universal testing instrument (Autograph AG-I model, manufactured by Shimadzu Corporation) under a compressive force of 9 kN and compression speed of 50 mm/min.

Example 8

9 g of powder amorphous tolvaptan that had been made amorphous together with hydroxypropylcellulose, 5.6 g of maltose monohydrate (Sunmalt-S, Sanwa Cornstarch Co., Ltd.), 4 g of calcium polycarbophil (Noveon CA-1, manufactured by Lubrizol Corporation), 0.5 g of carmellose (NS-300, manufactured by Nichirin Chemical Industries, Ltd.), 0.7 g of colloidal silicon dioxide (Aerosil 200, manufactured by Aerosil Co., Ltd., average particle diameter: 0.015 µm) and 0.2 g of magnesium stearate (plant origin, manufactured by Taihei Chemicals Limited, average particle diameter: 6 µm) were well mixed. The resulting mixture was formed into round tablets having a weight of about 200 mg and a diameter of 8 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 9

9 g of powder amorphous tolvaptan that had been made amorphous together with hydroxypropylcellulose, 3.9 g of trehalose (Trehalose P, manufactured by Asahi Kasei Chemicals Corporation), 3.6 g of calcium polycarbophil (Noveon CA-1, manufactured by Lubrizol Corporation), 0.9 g of carmellose (NS-300, manufactured by Nichirin Chemical Industries, Ltd.), 0.4 g of colloidal silicon dioxide (Aerosil 200, manufactured by Aerosil Co., Ltd., average particle diameter: 0.015 µm) and 0.2 g of magnesium stearate (plant origin, manufactured by Taihei Chemicals Limited, average particle diameter: 6 µm) were well mixed. The resulting mixture was formed into round tablets having a weight of about 180 mg and a diameter of 8 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 10

9 g of powder amorphous tolvaptan that had been made amorphous together with hydroxypropylcellulose, 3.9 g of maltitol (Maltisorb P90, manufactured by Roquette), 3.6 g of calcium polycarbophil (Noveon CA-1, manufactured by Lubrizol Corporation), 0.9 g of carmellose (NS-300, manufactured by Nichirin Chemical Industries, Ltd.), 0.4 g of colloidal silicon dioxide (Aerosil 200, manufactured by Aerosil Co., Ltd., average particle diameter: 0.015 µm) and 0.2 g of magnesium stearate (plant origin, manufactured by Taihei Chemicals Limited, average particle diameter: 6 µm) were well mixed. The resulting mixture was formed into round tablets having a weight of about 180 mg and a diameter of 8 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 11

9 g of powder amorphous tolvaptan that had been made amorphous together with hydroxypropylcellulose, 5.7 g of maltitol (Maltisorb P90, manufactured by Roquette), 1.8 g of calcium polycarbophil (Noveon CA-1, manufactured by Lubrizol Corporation), 0.9 g of carmellose (NS-300, manufactured by Nichirin Chemical Industries, Ltd.), 0.4 g of colloidal silicon dioxide (Aerosil 200, manufactured by Aerosil Co., Ltd., average particle diameter: 0.015 µm) and 0.2 g of magnesium stearate (plant origin, manufactured by Taihei Chemicals Limited, average particle diameter: 6 µm) were well mixed. The resulting mixture was formed into round tablets having a weight of about 180 mg and a diameter of 7.5 mm, and containing 60 mg of active ingredient; the tablets were prepared using a universal testing instrument (Autograph AG-I model, manufactured by Shimadzu Corporation) under a compressive force of 7 kN and compression speed of 100 mm/min.

Example 12

9 g of powder amorphous tolvaptan that had been made amorphous together with hydroxypropylcellulose, 2.1 g of maltitol (Maltisorb P90, manufactured by Roquette), 3.6 g of calcium polycarbophil (Noveon CA-1, manufactured by Lubrizol Corporation), 0.9 g of carmellose (NS-300, manufactured by Nichirin Chemical Industries, Ltd.), 1.8 g of crystalline cellulose (KG-802, manufactured by Asahi Kasei Chemicals Corporation), 0.4 g of colloidal silicon dioxide (Aerosil 200, manufactured by Aerosil Co., Ltd., average particle diameter: 0.015 µm) and 0.2 g of magnesium stearate (plant origin, manufactured by Taihei Chemicals Limited, average particle diameter: 6 µm) were well mixed. The resulting mixture was formed into round tablets having a weight of about 180 mg and a diameter of 7.5 mm, and containing 60 mg of active ingredient; the tablets were prepared using a universal testing instrument (Autograph AG-I model, manufactured by Shimadzu Corporation) under a compressive force of 10 kN and compression speed of 100 mm/min.

Example 13

9 g of powder amorphous tolvaptan that had been made amorphous together with hydroxypropylcellulose, 3.6 g of maltitol (Maltisorb P90, manufactured by Roquette), 3.6 g of calcium polycarbophil (Noveon CA-1, manufactured by Lubrizol Corporation), 0.9 g of carmellose (NS-300, manufactured by Nichirin Chemical Industries, Ltd.), 0.4 g of talc (MMR, manufactured by Asada Milling Co., Ltd., average particle diameter: 4 µm) and 0.2 g of magnesium stearate (plant origin, manufactured by Taihei Chemicals Limited, average particle diameter: 6 µm) were well mixed. The resulting mixture was formed into round tablets having a weight of about 177 mg and a diameter of 8 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 14

9 g of powder amorphous tolvaptan that had been made amorphous together with hydroxypropylcellulose, 3.6 of maltitol (Maltisorb P90, manufactured by Roquette), 3.6 g of calcium polycarbophil (Noveon CA-1, manufactured by Lubrizol Corporation), 0.9 g of carmellose (NS-300, manufactured by Nichirin Chemical Industries, Ltd.), 0.4 g of titanium oxide (A-HR, manufactured by Freund Corporation, average particle diameter: 1 µm) and 0.2 g of magnesium stearate (plant origin, manufactured by Taihei Chemicals Limited, average particle diameter: 6 µm) were well mixed. The resulting mixture was formed into round tablets having a weight of about 177 mg and a diameter of 8 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 15

360 g of powder amorphous tolvaptan that had been made amorphous together with hydroxypropylcellulose, 148 g of maltitol (Maltisorb P90, manufactured by Roquette), 120 g of calcium polycarbophil (Noveon CA-1, manufactured by Lubrizol Corporation), 36 g of carmellose (NS-300, manufactured by Nichirin Chemical Industries, Ltd.), 36 g of hydroxypropylcellulose (HCP-L fine powder, manufactured by Nippon Soda Co., Ltd.), 12 g of colloidal silicon dioxide (Aerosil 200, manufactured by Aerosil Co., Ltd., average particle diameter: 0.015 µm) and 8 g of magnesium stearate (plant origin, manufactured by Taihei Chemicals Limited, average particle diameter: 6 µm) were well mixed in a 3 L drum mixer. The resulting mixture was formed into round tablets having a weight of about 180 mg and a diameter of 7.5 mm, and containing 60 mg of active ingredient; the tablets were prepared using a rotary tableting machine (12HUK-AWC, manufactured by Kikusui Seisakusho Ltd.) under a tableting pressure of 1,100 kg and rotational speed of 40 rpm.

Example 16

360 g of powder amorphous tolvaptan that had been made amorphous together with hydroxypropylcellulose, 160 g of maltitol (Maltisorb P90, manufactured by Roquette), 120 g of calcium polycarbophil (Noveon CA-1, manufactured by Lubrizol Corporation), 24 g of carmellose (NS-300, manufactured by Nichirin Chemical Industries, Ltd.), 36 g of hydroxypropylcellulose (HCP-L fine powder, manufactured by Nippon Soda Co., Ltd.), 12 g of colloidal silicon dioxide (Aerosil 200, manufactured by Aerosil Co., Ltd., average particle diameter: 0.015 µm) and 8 g of magnesium stearate (plant origin, manufactured by Taihei Chemicals Limited, average particle diameter: 6 µm) were well mixed in a 3 L drum mixer. The resulting mixture was formed into round tablets having a weight of about 180 mg and a diameter of 7.5 mm, and containing 60 mg of active ingredient; the tablets were prepared using a rotary tableting machine (12HUK-AWC, manufactured by Kikusui Seisakusho Ltd.) under a tableting pressure of 1,100 kg and rotational speed of 40 rpm.

Example 17

9 g of powder amorphous tolvaptan that had been made amorphous together with hydroxypropylcellulose, 3.7 g of lactitol (lactitol LC-1, manufactured by Nikken Chemical and Synthetic Industry Co., Ltd., 3 g of calcium polycarbophil (Noveon CA-1, manufactured by Lubrizol Corporation), 0.9 g of carmellose (NS-300, manufactured by Nichirin Chemical Industries, Ltd.), 0.9 g of hydroxypropylcellulose (HCP-L fine powder, manufactured by Nippon Soda Co., Ltd.), 0.3 g of colloidal silicon dioxide (Aerosil 200, manufactured by Aerosil Co., Ltd., average particle diameter: 0.015 µm) and 0.2 g of magnesium stearate (plant origin, manufactured by Taihei Chemicals Limited, average particle diameter: 6 µm) were well mixed. The resulting mixture was formed into round tablets having a weight of about 180 mg and a diameter of 7.5 mm, and containing 60 mg of active ingredient; the tablets were prepared using a universal testing instrument (Autograph AG-I model, manufactured by Shimadzu Corporation) under a compressive force of 7 kN and compression speed of 100 mm/min.

Example 18

9 g of powder amorphous tolvaptan that had been made amorphous together with hydroxypropylcellulose, 3.1 g of maltitol (Maltisorb P90, manufactured by Roquette), 3 g of calcium polycarbophil (Noveon CA-1, manufactured by Lubrizol Corporation), 0.9 g of carmellose (NS-300, manufactured by Nichirin Chemical Industries, Ltd.), 0.9 g of hydroxypropylcellulose (HCP-L fine powder, manufactured by Nippon Soda Co., Ltd.), 0.9 g of colloidal silicon dioxide (Aerosil 200, manufactured by Aerosil Co., Ltd., average particle diameter: 0.015 µm) and 0.2 g of magnesium stearate (plant origin, manufactured by Taihei Chemicals Limited, average particle diameter: 6 µm) were well mixed. The resulting mixture was formed into round tablets having a weight of about 180 mg and a diameter of 7.5 mm, and containing 60 mg of active ingredient; the tablets were prepared using a universal testing instrument (Autograph AG-I model, manufactured by Shimadzu Corporation) under a compressive force of 7 kN and compression speed of 100 mm/min.

Example 19

Theophylline (theophylline as defined in the Japanese Pharmacopoeia, manufactured by Shiratori Pharmaceutical Co., Ltd., 10 g), 0.75 g of maltitol (Maltisorb P90, manufactured by Roquette), 2 g of calcium polycarbophil (Noveon CA-1, manufactured by Lubrizol Corporation), 0.3 g of carmellose (NS-300, manufactured by Nichirin Chemical Industries, Ltd.), 1.5 g of hydroxypropylcellulose (HCP-L fine powder, manufactured by Nippon Soda Co., Ltd.), 0.3 g of colloidal silicon dioxide (Aerosil 200, manufactured by Aerosil Co., Ltd., average particle diameter: 0.015 µm) and 0.2 g of magnesium stearate (plant origin, manufactured by Taihei Chemicals Limited, average particle diameter: 6 µm) were well mixed. The resulting mixture was formed into round tablets having a weight of about 300 mg and a diameter of 8.5 mm, and containing 200 mg of active ingredient; the tablets were prepared using a universal testing instrument (Autograph AG-I model, manufactured by Shimadzu Corporation) under a compressive force of 8 kN and compression speed of 100 mm/min.

Example 20

5.25 g of cilostazol that had been mixed with sodium lauryl sulfate and pulverized into fine particles (cilostazol/sodium lauryl sulfate=10/0.5, 5 g calculated as cilostazol), 3.15 g of maltitol (Maltisorb P90, manufactured by Roquette), 3 g of calcium polycarbophil (Noveon CA-1, manufactured by Lubrizol Corporation), 0.15 g of carmellose (NS-300, manufactured by Nichirin Chemical Industries, Ltd.), 1.5 g of crystalline cellulose (KG-802, manufactured by Asahi Kasei Chemicals Corporation), 1.5 g of hydroxypropylcellulose (HPC-L fine powder, manufactured by Nippon Soda Co., Ltd.), 0.3 g of titanium oxide (A-HR, manufactured by Freund Corporation, average particle diameter: 1 µm) and 0.15 g of magnesium stearate (plant origin, manufactured by Taihei Chemicals Limited, average particle diameter: 6 µm) were well mixed. The resulting mixture was formed into round tablets having a weight of about 300 mg and a diameter of 8.5 mm, and containing 100 mg of active ingredient; the tablets were prepared using a universal testing instrument (Autograph AG-I model, manufactured by Shimadzu Corporation) under a compressive force of 9 kN and compression speed of 100 mm/min.

Example 21

9 g of powder amorphous tolvaptan that had been made amorphous together with hydroxypropylcellulose, 20.5 g of maltose monohydrate (Sunmalt-S, Sanwa Cornstarch Co., Ltd.), 8 g of calcium polycarbophil (Noveon CA-1, manufactured by Lubrizol Corporation), 2 g of carmellose (NS-300, manufactured by Nichirin Chemical Industries, Ltd.), 0.4 g of colloidal silicon dioxide (Aerosil 200, manufactured by Aerosil Co., Ltd., average particle diameter: 0.015 µm) and 0.1 g of magnesium stearate (plant origin, manufactured by Taihei Chemicals Limited, average particle diameter: 6 µm) were well mixed. The resulting mixture was formed into round tablets having a weight of about 400 mg and a diameter of 10.5 mm, and containing 60 mg of active ingredient; the tablets were prepared using a universal testing instrument (Autograph AG-I model, manufactured by Shimadzu Corporation) under a compressive force of 17.2 kN and compression speed of 50 mm/min.

Example 22

9 g of powder amorphous tolvaptan that had been made amorphous together with hydroxypropylcellulose, 13.1 g of maltose monohydrate (Sunmalt-S, Sanwa Cornstarch Co., Ltd.), 6 g of calcium polycarbophil (Noveon CA-1, manufactured by Lubrizol Corporation), 1.5 g of carmellose (NS-300, manufactured by Nichirin Chemical Industries, Ltd.), 0.3 g of colloidal silicon dioxide (Aerosil 200, manufactured by Aerosil Co., Ltd., average particle diameter: 0.015 µm) and 0.1 g of magnesium stearate (plant origin, manufactured by Taihei Chemicals Limited, average particle diameter: 6 µm) were well mixed. The resulting mixture was formed into round tablets having a weight of about 300 mg and a diameter of 9 mm, and containing 60 mg of active ingredient; the tablets were prepared using a universal testing instrument (Autograph AG-I model, manufactured by Shimadzu Corporation) under a compressive force of 12.7 kN and compression speed of 50 mm/min.

Example 23

900 g of powder amorphous tolvaptan that had been made amorphous together with hydroxypropylcellulose, 600 g of maltitol (Maltisorb P90, manufactured by Roquette), 300 g of calcium polycarbophil (Noveon CA-1, manufactured by Lubrizol Corporation), 30 g of carmellose (NS-300, manufactured by Nichirin Chemical Industries, Ltd.), 240 g of hydroxypropylcellulose (HCP-L fine powder, manufactured by Nippon Soda Co., Ltd.), 150 g of ethylcellulose (Ethocel SDT 10 c.p.s. FP, manufactured by the Dow Chemical Company, average particle diameter: 5 µm), 150 g of talc (PKP-81, manufactured by Fuji Talc Industrial Co., Lt., average particle diameter: 14 µm) and 6 g of colloidal silicon dioxide (Aerosil 200, manufactured by Aerosil Co., Ltd., average particle diameter: 0.015 µm) were well mixed using a high-shear mixer granulator (FM-VG-25P, manufactured by Powrex Corporation). The mixture was then mixed with 24 g of magnesium stearate (plant origin, manufactured by Taihei Chemicals Limited, average particle diameter: 6 µm) in a drum mixer, obtaining powder for tableting. The resulting powder was formed into round tablets having a weight of about 80 mg and a diameter of 6 mm, and containing 20 mg of active ingredient; the tablets were prepared using a rotary tableting machine (12HUK-AWC, manufactured by Kikusui Seisakusho Ltd.) under a tableting pressure of 900 kg and rotational speed of 50 rpm.

Example 24

900 g of powder amorphous tolvaptan that had been made amorphous together with hydroxypropylcellulose, 540 g of maltitol (Maltisorb P90, manufactured by Roquette), 300 g of calcium polycarbophil (Noveon CA-1, manufactured by Lubrizol Corporation), 90 g of carmellose (NS-300, manufactured by Nichirin Chemical Industries, Ltd.), 240 g of hydroxypropylcellulose (HCP-L fine powder, manufactured by Nippon Soda Co., Ltd.), 150 g of ethylcellulose (Ethocel SDT 10 c.p.s. FP, manufactured by the Dow Chemical Company, average particle diameter: 5 µm), 150 g of talc (PKP-81, manufactured by Fuji Talc Industrial Co., Lt., average particle diameter: 14 µm) and 6 g of colloidal silicon dioxide (Aerosil 200, manufactured by Aerosil Co., Ltd., average particle diameter: 0.015 µm) were well mixed in a high-shear mixer granulator (FM-VG-25P, manufactured by Powrex Corporation). The mixture was then mixed with 24 g of magnesium stearate (plant origin, manufactured by Taihei Chemicals Limited, average particle diameter: 6 µm) in a drum mixer, obtaining powder for tableting. The resulting mixture was formed into round tablets having a weight of about 80 mg and a diameter of 6 mm, and containing 20 mg of active ingredient; the tablets were prepared using an rotary tableting machine (12HUK-AWC, manufactured by Kikusui Seisakusho Ltd.) under a tableting pressure of 900 kg and rotational speed of 50 rpm.

Example 25

900 g of powder amorphous tolvaptan that had been made amorphous together with hydroxypropylcellulose, 480 g of maltitol (Maltisorb P90, manufactured by Roquette), 300 g of calcium polycarbophil (Noveon CA-1, manufactured by Lubrizol Corporation), 150 g of carmellose (NS-300, manufactured by Nichirin Chemical Industries, Ltd.), 240 g of hydroxypropylcellulose (HCP-L fine powder, manufactured by Nippon Soda Co., Ltd.), 150 g of ethylcellulose (Ethocel SDT 10 c.p.s. FP, manufactured by the Dow Chemical Company, average particle diameter: 5 µm), 150 g of talc (PKP-81, manufactured by Fuji Talc Industrial Co., Lt., average particle diameter: 14 µm) and 6 g of colloidal silicon dioxide (Aerosil 200, manufactured by Aerosil Co., Ltd., average particle diameter: 0.015 µm) were well mixed in a high-shear mixer granulator (FM-VG-25P, manufactured by Powrex Corporation). The mixture was then mixed with 24 g of magnesium stearate (plant origin, manufactured by Taihei Chemicals Limited, average particle diameter: 6 μm) in a drum mixer, obtaining powder for tableting. The resulting mixture was formed into round tablets having a weight of about 80 mg and a diameter of 6 mm, and containing 20 mg of active ingredient; the tablets were prepared using a rotary tableting machine (12HUK-AWC, manufactured by Kikusui Seisakusho Ltd.) under a tableting pressure of 900 kg and rotational speed of 50 rpm.

Example 26

6 g of powder amorphous tolvaptan that had been made amorphous together with hydroxypropylcellulose, 3.6 g of maltitol (Maltisorb P90, manufactured by Roquette), 2 g of calcium polycarbophil (Noveon CA-1, manufactured by Lubrizol Corporation), 0.2 g of carmellose (NS-300, manufactured by Nichirin Chemical Industries, Ltd.), 1.6 g of hydroxypropylcellulose (HCP-L fine powder, manufactured by Nippon Soda Co., Ltd.), 1.2 g of ethylcellulose (Ethocel SDT 10 c.p.s. FP, manufactured by the Dow Chemical Company, average particle diameter: 5 μm), 1.2 g of colloidal silicon dioxide (Aerosil 200, manufactured by Aerosil Co., Ltd., average particle diameter: 0.015 μm) and 0.2 g of magnesium stearate (plant origin, manufactured by Taihei Chemicals Limited, average particle diameter: 6 μm) were well mixed. The resulting mixture was formed into round tablets having a weight of about 80 mg and a diameter of 5.5 mm, and containing 20 mg of active ingredient; the tablets were prepared using a universal testing instrument (Autograph AG-I model, manufactured by Shimadzu Corporation) under a compressive force of 5 kN and compression speed of 100 mm/min.

Example 27

300 g of powder amorphous tolvaptan that had been made amorphous together with hydroxypropylcellulose, 202 g of maltitol (Maltisorb P90, manufactured by Roquette), 100 g of calcium polycarbophil (Noveon CA-1, manufactured by Lubrizol Corporation), 10 g of carmellose (NS-300, manufactured by Nichirin Chemical Industries, Ltd.), 80 g of hydroxypropylcellulose (HCP-L fine powder, manufactured by Nippon Soda Co., Ltd.), 50 g of ethylcellulose (Ethocel SDT 10 c.p.s. FP, manufactured by the Dow Chemical Company, average particle diameter: 5 μm), 50 g talc (PKP-81, manufactured by Fuji Talc Industrial Co., Lt., average particle diameter: 14 μm) and 8 g of magnesium stearate (plant origin, manufactured by Taihei Chemicals Limited, average particle diameter: 6 μm) were well mixed in a 5 L of high-shear mixer granulator (FM-VG-05, manufactured by Powrex Corporation). The resulting mixture was formed into round tablets having a weight of about 80 mg and a diameter of 5.5 mm, and containing 20 mg of active ingredient; the tablets were prepared using a rotary tableting machine (12HUK-AWC, manufactured by Kikusui Seisakusho Ltd.) under a tableting pressure of 800 kg and rotational speed of 50 rpm.

Example 28

6 g of powder amorphous tolvaptan that had been made amorphous together with hydroxypropylcellulose, 3 g of maltitol (Maltisorb P90, manufactured by Roquette), and 3 g of calcium polycarbophil (Noveon CA-1, manufactured by Lubrizol Corporation) were well mixed. The resulting mixture was formed into round tablets having a weight of about 150 mg and a diameter of 7.5 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 29

6 g of powder amorphous tolvaptan that had been made amorphous together with hydroxypropylcellulose, 3 g of D-mannitol (Pearlitol 200SD, manufactured by Roquette), and 3 g of calcium polycarbophil (Noveon CA-1, manufactured by Lubrizol Corporation) were well mixed. The resulting mixture was formed into round tablets having a weight of about 150 mg and a diameter of 7.5 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 30

6 g of powder amorphous tolvaptan that had been made amorphous together with hydroxypropylcellulose, 3 g of isomalt (galenIQ 721, manufactured by Palatinit GmbH), and 3 g of calcium polycarbophil (Noveon CA-1, manufactured by Lubrizol Corporation) were well mixed. The resulting mixture was formed into round tablets having a weight of about 150 mg and a diameter of 7.5 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 31

9 g of amorphous tolvaptan (9 g) that had been made amorphous together with hydroxypropylcellulose, 2.25 g of maltitol (Maltisorb P90, manufactured by Roquette), 3 g of calcium polycarbophil (Noveon CA-1, manufactured by Lubrizol Corporation) and 0.75 g of carmellose (NS-300, manufactured by Nichirin Chemical Industries, Ltd.) were well mixed. The resulting mixture was formed into round tablets having a weight of about 150 mg and a diameter of 7.5 mm, and containing 60 mg of active ingredient; the tablets were prepared using a universal testing instrument (Autograph AG-I model, manufactured by Shimadzu Corporation) under a compressive force of 8 kN and compression speed of 50 mm/min.

Example 32

3 g of powder amorphous tolvaptan that had been made amorphous together with hydroxypropylcellulose, 3.5 g of maltitol (Maltisorb P90, manufactured by Roquette), 2 g of calcium polycarbophil (Noveon CA-1, manufactured by Lubrizol Corporation), 0.6 g of carmellose (NS-300, manufactured by Nichirin Chemical Industries, Ltd.), 1 g of hydroxypropylcellulose (HCP-L fine powder, manufactured by Nippon Soda Co., Ltd.), 0.6 g of ethylcellulose (Ethocel SDT 10 c.p.s. FP, manufactured by the Dow Chemical Company, average particle diameter: 5 μm), 0.2 g of colloidal silicon dioxide (Aerosil 200, manufactured by Aerosil Co., Ltd., average particle diameter: 0.015 μm) and 0.1 g of magnesium stearate (plant origin, manufactured by Taihei Chemicals Limited, average particle diameter: 6 μm) were well mixed. The resulting mixture was formed into round tablets having a weight of about 100 mg and a diameter of 6 mm, and containing 20 mg of active ingredient; the tablets were prepared using a universal testing instrument (Autograph AG-I model, manufactured by Shimadzu Corporation) under a compressive force of 6 kN and compression speed of 100 mm/min.

Comparative Example 1

9 g of powder amorphous tolvaptan that had been made amorphous together with hydroxypropylcellulose, 4.9 g of maltitol (Maltisorb P90, manufactured by Roquette), 0.8 g of carmellose (NS-300, manufactured by Nichirin Chemical Industries, Ltd.), 0.3 g of colloidal silicon dioxide (Aerosil 200, manufactured by Aerosil Co., Ltd., average particle diameter: 0.015 µm), and 0.1 g of magnesium stearate (plant origin, manufactured by Taihei Chemicals Limited, average particle diameter: 6 µm) were well mixed. The resulting mixture was formed into round tablets having a weight of about 150 mg and a diameter of 7.5 mm, and containing 60 mg of active ingredient; the tablets were prepared using a universal testing instrument (Autograph AG-I model, manufactured by Shimadzu Corporation) under a compressive force of 8 kN and compression speed of 100 mm/min.

Comparative Example 2

9 g of powder amorphous tolvaptan that had been made amorphous together with hydroxypropylcellulose, 3 g of carboxyvinyl polymer (Carbopol 71GNF, manufactured by Lubrizol Corporation), 3.7 g of maltitol (Maltisorb P90, manufactured by Roquette), 0.9 g of carmellose (NS-300, manufactured by Nichirin Chemical Industries, Ltd.), 0.9 g of hydroxypropylcellulose (HPC-L, manufactured by Nippon Soda Co., Ltd.), 0.3 g of colloidal silicon dioxide (Aerosil 200, manufactured by Aerosil Co., Ltd., average particle diameter: 0.015 µm), and 0.2 g of magnesium stearate (plant origin, manufactured by Taihei Chemicals Limited, average particle diameter: 6 µm) were weighed and well mixed. The resulting mixture was formed into round tablets having a weight of about 180 mg and a diameter of 7.5 mm, and containing 60 mg of active ingredient; the tablets were prepared using a universal testing instrument (Autograph AG-I model, manufactured by Shimadzu Corporation) under a compressive force of 7 kN and compression speed of 100 mm/min.

Comparative Example 3

9 g of powder amorphous tolvaptan that had been made amorphous together with hydroxypropylcellulose, 3 g of polyvinyl alcohol (Gohsenol AH-17, manufactured by Nippon Synthetic Chemical Industries), 3.7 g of maltitol (Maltisorb P90, manufactured by Roquette), 0.9 g of carmellose (NS-300, manufactured by Nichirin Chemical Industries, Ltd.), 0.9 g of hydroxypropylcellulose (HPC-L, manufactured by Nippon Soda Co., Ltd.), 0.3 g of colloidal silicon dioxide (Aerosil 200, manufactured by Aerosil Co., Ltd., average particle diameter: 0.015 µm), and 0.2 g of magnesium stearate (plant origin, manufactured by Taihei Chemicals Limited, average particle diameter: 6 µm) were weighed and well mixed. The resulting mixture was formed into round tablets having a weight of about 180 mg and a diameter of 7.5 mm, and containing 60 mg of active ingredient; the tablets were prepared using a universal testing instrument (Autograph AG-I model, manufactured by Shimadzu Corporation) under a compressive force of 7 kN and compression speed of 100 mm/min.

Comparative Example 4

9 g of powder amorphous tolvaptan that had been made amorphous together with hydroxypropylcellulose, 3 g of polycarbophil (Noveon AA-1, manufactured by Lubrizol Corporation), 3.7 g of maltitol (Maltisorb P90, manufactured by Roquette), 0.9 g of carmellose (NS-300, manufactured by Nichirin Chemical Industries, Ltd.), 0.9 g of hydroxypropylcellulose (HPC-L, manufactured by Nippon Soda Co., Ltd.), 0.3 g of colloidal silicon dioxide (Aerosil 200, manufactured by Aerosil Co., Ltd., average particle diameter: 0.015 µm), and 0.2 g of magnesium stearate (plant origin, manufactured by Taihei Chemicals Limited, average particle diameter: 6 µm) were weighed and well mixed. The resulting mixture was formed into round tablets having a weight of about 180 mg and a diameter of 7.5 mm, and containing 60 mg of active ingredient; the tablets were prepared using a universal testing instrument (Autograph AG-I model, manufactured by Shimadzu Corporation) under a compressive force of 7 kN and compression speed of 100 mm/min.

Comparative Example 5

9 g of powder amorphous tolvaptan that had been made amorphous together with hydroxypropylcellulose, 4 g of calcium polycarbophil (Noveon CA-1, manufactured by Lubrizol Corporation), 0.8 g of carmellose (NS-300, manufactured by Nichirin Chemical Industries, Ltd.), 0.3 g of colloidal silicon dioxide (Aerosil 200, manufactured by Aerosil Co., Ltd., average particle diameter: 0.015 µm) and 0.1 g of magnesium stearate (plant origin, manufactured by Taihei Chemicals Limited, average particle diameter: 6 µm) were well mixed. The resulting mixture was formed into round tablets having a weight of about 142 mg and a diameter of 6.5 mm, and containing 60 mg of active ingredient; the tablets were prepared using a universal testing instrument (Autograph AG-I model, manufactured by Shimadzu Corporation) under a compressive force of 7 kN and compression speed of 50 mm/min.

Test Example 1

The round tablets produced in Examples 1-32 and Comparative Examples 1-5 were visually observed to determine the patterns of their change in shape during the dissolution test: a gradual disintegration-type wherein the preparation gradually disintegrated while releasing solid particles from the surface layer portion; an internal disintegration-type; a hydrogel-type (swelling-type); or an insoluble matrix-type.

Figure 2:
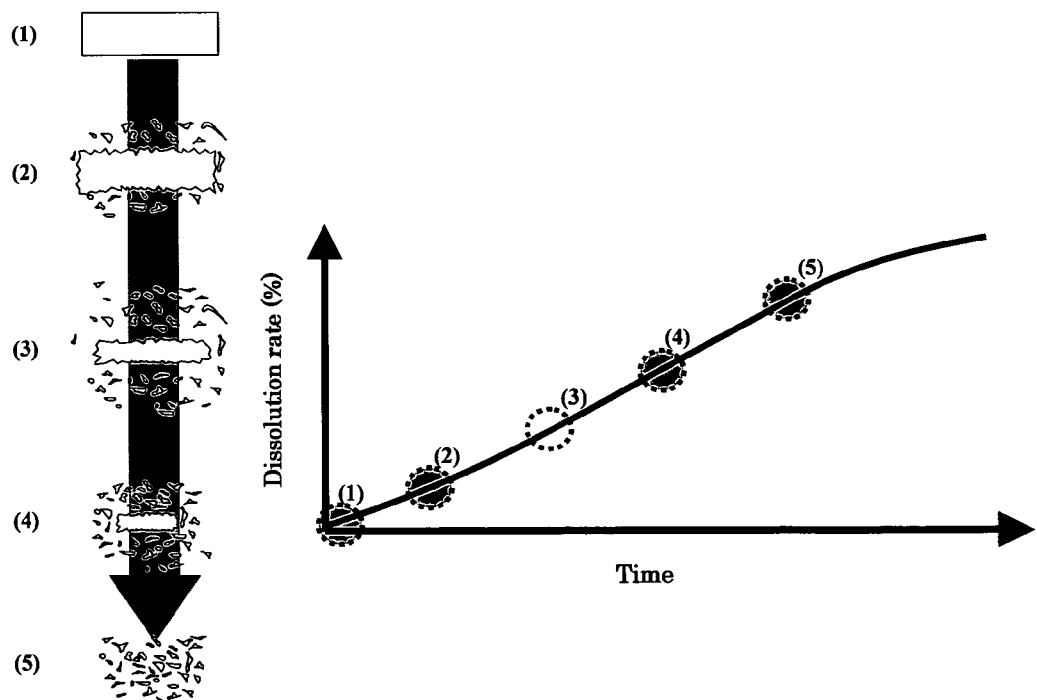
FIG. 2 represents a graph showing the relationship between the change in shape of the tablet and the pharmacologically active substance-release behavior in the dissolution test of Test Example 2.

FIG. 2 shows the relationship between the change in shape of the solid pharmaceutical preparation of the present invention with time and the pharmacologically active substance-release behavior. As shown in FIG. 2, the solid pharmaceutical preparation of the present invention was eroded while gradually forming solid substance peeled off from the surface layer portion during the steps (1)-(5) of releasing the pharmacologically active substance. Eventually, the tablets were totally disintegrated, and only the peeled-off solid substance remained. The peeled-off solid substance formed during the dissolution of the preparation did not remain in this state, but dissolved or collapsed while releasing the pharmacologically active substance, and eventually left only transparent gel beads as a residue. These gel beads form a water-absorbing polymer that swells and gelates with the absorption of water.

Table 3 shows the results of the visual observation, wherein all of the preparations produced in the Examples exhibited gradual disintegration-type pharmacologically active substance-release behavior. In contrast, the round tablets produced in Comparative Example 1 exhibited the insoluble matrix-type dissolution behavior, and the shape of the preparation remained unchanged even after the dissolution test. A hydrated gel layer was formed on the surface layer portion of the round tablets produced in Comparative Examples 2 and 4, which is observed in a preparation of the hydrogel-type. The round tablets produced in Comparative Examples 2 and 4 did not exhibit the gradual disintegration behavior. The round tablets produced in Comparative Examples 3 exhibited the internal disintegration-type dissolution behavior; i.e., the preparations were collapsed to a great extent by the water that rapidly penetrated into the preparation. The round tablets produced in Comparative Example 5 exhibited a vertical breaking-type dissolution behavior which resulted in strong erosion from the side portion. In other words, the round tablets produced in Comparative Example 5 were not gradual disintegration-type preparations.

Test Example 2

Dissolution tests using each of the round tablets produced in the Examples were conducted in an acidic test fluid (Test Liquid C) and a neutral test fluid (Test Liquid D). The conditions of the dissolution test were as shown below.

Test Liquid C (acidic condition): 900 ml of solution in total, prepared by adding polysorbate 80 to a diluted McIlvaine buffer solution (pH4.0) in such a manner that the concentration of the polysorbate 80 became 1 w/v %.

Test Liquid D (neutral condition): 900 ml of solution in total, prepared by adding polysorbate 80 to the second fluid (pH 6.8) of the Japanese Pharmacopoeia, Dissolution Test, in such a manner that the concentration of the polysorbate 80 became 1 w/v %.

Using the dissolution test system NTR-6200A (manufactured by Toyama Sangyo Co., Ltd.), an dissolution test was conducted according to the Japanese Pharmacopoeia, Dissolution Test (2nd Method, Paddle Method) to dissolve tolvaptan from the solid preparations. The test was conducted at a paddle rotation of 100 rpm, with the measurement wavelength at 268 nm and 350 nm.

(1) Pharmacologically Active Substance Release Rate

The round tablets produced in Examples 1-3 exhibited the correlation coefficients of the regression equation of not less than 0.90 both in the tests conducted in the acidic solutions and in the tests conducted in the neutral solutions. The correlation coefficients of the regression equation were obtained by conducting the linear regression using the time lapsed in the dissolution test and the data of the dissolution rate from the first sampling time to the sampling time when not less than 85% of the pharmacologically active substance was dissolved the first time. It was confirmed that the round tablets released the pharmacologically active substance at a fixed rate; and, judging from the change of the dissolution rate of the pharmacologically active substance with time, the preparations of Examples 1-32 all exhibited the sustained-release behavior of the pharmacologically active substance. Tables 3-6 show the results.

TABLE 3

| Ex. | | 0.5 h | 1 h | 2 h | 3 h | 4 h | 6 h | 8 h | 10 h | 12 h | 14 h | 16 h | Correlation coefficient of fixed release rate | Releasing mechanism (Change in shape) |
|---|---|---|---|---|---|---|---|---|---|---|---|---|---|---|
| | | Dissolution Rate (%) (Upper Column: Acidic Solution, Lower Column: Neutral Solution) | | | | | | | | | | | | |
| 1 | Acidic Solution | 0 | 1 | 4 | 9 | 15 | 29 | 43 | 56 | 68 | 78 | 85 | 0.994 | Gradual disintegration-type |
| | Neutral Solution | 0 | 2 | 6 | 14 | 23 | 43 | 64 | 82 | 96 | | | 0.993 | |
| 2 | Acidic Solution | 0 | 1 | 2 | 5 | 8 | 15 | 23 | 31 | 39 | 46 | 52 | 0.994 | Gradual disintegration-type |
| | Neutral Solution | 1 | 1 | 3 | 6 | 10 | 19 | 29 | 40 | 50 | 60 | 71 | 0.991 | |
| 3 | Acidic Solution | 28 | 43 | 68 | 87 | 94 | | | | | | | 0.957 | Gradual disintegration-type |
| | Neutral Solution | 8 | 15 | 28 | 46 | 68 | 99 | | | | | | 0.995 | |
| 4 | Acidic Solution | 2 | 4 | 8 | 13 | 18 | 29 | 38 | 45 | 52 | 58 | 63 | 0.989 | Gradual disintegration-type |
| | Neutral Solution | 2 | 4 | 14 | 33 | 56 | 90 | 99 | 101 | | | | 0.968 | |
| 5 | Acidic Solution | 2 | 5 | 14 | 26 | 38 | 65 | 84 | 92 | | | | 0.984 | Gradual disintegration-type |
| | Neutral Solution | 2 | 4 | 17 | 34 | 53 | 85 | 97 | | | | | 0.980 | |
| 6 | Acidic Solution | 24 | 38 | 60 | 81 | 90 | | | | | | | 0.975 | Gradual disintegration-type |
| | Neutral Solution | 27 | 42 | 69 | 91 | 96 | | | | | | | 0.966 | |
| 7 | Acidic Solution | 2 | 5 | 13 | 23 | 33 | 56 | 78 | 87 | 90 | | | 0.991 | Gradual disintegration-type |
| | Neutral Solution | 2 | 4 | 10 | 21 | 33 | 63 | 88 | 95 | | | | 0.983 | |
| 8 | Acidic Solution | 1 | 4 | 11 | 20 | 30 | 52 | 72 | 85 | 90 | | | 0.995 | Gradual disintegration-type |
| | Neutral Solution | 1 | 3 | 9 | 18 | 28 | 55 | 82 | 97 | | | | 0.987 | |
| 9 | Acidic Solution | 3 | 7 | 16 | 26 | 38 | 64 | 85 | 93 | | | | 0.996 | Gradual disintegration-type |
| | Neutral Solution | 2 | 5 | 13 | 25 | 40 | 74 | 97 | | | | | 0.988 | |

TABLE 3-continued

| Ex. | | Dissolution Rate (%) (Upper Column: Acidic Solution, Lower Column: Neutral Solution) | | | | | | | | | | | Correlation coefficient of fixed release rate | Releasing mechanism (Change in shape) |
|---|---|---|---|---|---|---|---|---|---|---|---|---|---|---|
| | | 0.5 h | 1 h | 2 h | 3 h | 4 h | 6 h | 8 h | 10 h | 12 h | 14 h | 16 h | | |
| 10 | Acidic Solution | 3 | 7 | 17 | 28 | 42 | 69 | 88 | 94 | | | | 0.996 | Gradual disintegration-type |
| | Neutral Solution | 2 | 4 | 11 | 22 | 36 | 65 | 88 | 98 | | | | 0.988 | |

TABLE 4

| Ex. | | Dissolution Rate (%) (Upper Column: Acidic Solution, Lower Column: Neutral Solution) | | | | | | | | | | | Correlation coefficient of fixed release rate | Releasing mechanism (Change in shape) |
|---|---|---|---|---|---|---|---|---|---|---|---|---|---|---|
| | | 0.5 h | 1 h | 2 h | 3 h | 4 h | 6 h | 8 h | 10 h | 12 h | 14 h | 16 h | | |
| 11 | Acidic Solution | 1 | 4 | 11 | 20 | 30 | 54 | 77 | 93 | | | | 0.994 | Gradual disintegration-type |
| | Neutral Solution | 1 | 3 | 8 | 17 | 28 | 54 | 81 | 99 | | | | 0.987 | |
| 12 | Acidic Solution | 1 | 4 | 10 | 17 | 25 | 41 | 58 | 74 | 86 | 92 | | 0.998 | Gradual disintegration-type |
| | Neutral Solution | 1 | 4 | 8 | 15 | 23 | 41 | 62 | 80 | 93 | 100 | | 0.993 | |
| 13 | Acidic Solution | 1 | 4 | 11 | 20 | 30 | 54 | 77 | 94 | | | | 0.995 | Gradual disintegration-type |
| | Neutral Solution | 1 | 4 | 8 | 17 | 28 | 54 | 81 | 99 | | | | 0.986 | |
| 14 | Acidic Solution | 2 | 5 | 14 | 25 | 36 | 60 | 83 | 96 | | | | 0.995 | Gradual disintegration-type |
| | Neutral Solution | 2 | 4 | 11 | 22 | 34 | 62 | 86 | 99 | | | | 0.988 | |
| 15 | Acidic Solution | 2 | 5 | 12 | 22 | 31 | 52 | 72 | 88 | 94 | | | 0.998 | Gradual disintegration-type |
| | Neutral Solution | 1 | 3 | 10 | 20 | 32 | 54 | 77 | 93 | 99 | | | 0.995 | |
| 16 | Acidic Solution | 1 | 2 | 6 | 11 | 17 | 30 | 45 | 59 | 71 | 82 | 90 | 0.995 | Gradual disintegration-type |
| | Neutral Solution | 1 | 2 | 5 | 11 | 17 | 32 | 48 | 62 | 74 | 85 | 94 | 0.994 | |
| 17 | Acidic Solution | 4 | 8 | 16 | 24 | 31 | 47 | 63 | 77 | 87 | 91 | | 0.997 | Gradual disintegration-type |
| | Neutral Solution | 3 | 7 | 14 | 23 | 32 | 51 | 71 | 87 | 91 | 98 | | 0.999 | |
| 18 | Acidic Solution | 3 | 7 | 19 | 32 | 46 | 73 | 91 | 97 | | | | 0.996 | Gradual disintegration-type |
| | Neutral Solution | 2 | 6 | 16 | 29 | 44 | 73 | 93 | 99 | | | | 0.995 | |
| 19 | Acidic Solution | 15 | 30 | 55 | 75 | 91 | 99 | | | | | | 0.988 | Gradual disintegration-type |
| | Neutral Solution | 20 | 36 | 61 | 78 | 92 | 100 | | | | | | 0.978 | |
| 20 | Acidic Solution | 13 | 27 | 49 | 67 | 85 | 96 | | | | | | 0.994 | Gradual disintegration-type |
| | Neutral Solution | 17 | 29 | 51 | 77 | 94 | 96 | | | | | | 0.996 | |

TABLE 5

| Ex. | | Dissolution Rate (%) (Upper Column: Acidic Solution, Lower Column: Neutral Solution) | | | | | | | | | | | Correlation coefficient of fixed release rate | Releasing mechanism (Change in shape) |
|---|---|---|---|---|---|---|---|---|---|---|---|---|---|---|
| | | 0.5 h | 1 h | 2 h | 3 h | 4 h | 6 h | 8 h | 10 h | 12 h | 14 h | 16 h | | |
| 21 | Acidic Solution | 10 | 30 | 81 | 90 | | | | | | | | 0.922 | Gradual disintegration-type |
| | Neutral Solution | 14 | 47 | 93 | | | | | | | | | 0.991 | |
| 22 | Acidic Solution | 4 | 10 | 27 | 46 | 65 | 90 | | | | | | 0.968 | Gradual disintegration-type |
| | Neutral Solution | 5 | 11 | 32 | 57 | 82 | 96 | | | | | | 0.957 | |

TABLE 5-continued

| Ex. | | Dissolution Rate (%) (Upper Column: Acidic Solution, Lower Column: Neutral Solution) | | | | | | | | | | | Correlation coefficient of fixed release rate | Releasing mechanism (Change in shape) |
|---|---|---|---|---|---|---|---|---|---|---|---|---|---|---|
| | | 0.5 h | 1 h | 2 h | 3 h | 4 h | 6 h | 8 h | 10 h | 12 h | 14 h | 16 h | | |
| 23 | Acidic Solution | 1 | 2 | 4 | 8 | 12 | 23 | 36 | 50 | 65 | 77 | 85 | 0.989 | Gradual disintegration-type |
| | Neutral Solution | 1 | 2 | 5 | 9 | 13 | 24 | 40 | 56 | 71 | 85 | 95 | 0.989 | |
| 24 | Acidic Solution | 1 | 3 | 8 | 14 | 21 | 40 | 59 | 77 | 88 | 94 | | 0.992 | Gradual disintegration-type |
| | Neutral Solution | 1 | 2 | 6 | 12 | 21 | 42 | 66 | 85 | 97 | | | 0.987 | |
| 25 | Acidic Solution | 2 | 5 | 13 | 23 | 35 | 61 | 82 | 93 | | | | 0.990 | Gradual disintegration-type |
| | Neutral Solution | 1 | 3 | 10 | 22 | 36 | 68 | 90 | 97 | | | | 0.986 | |
| 26 | Acidic Solution | 1 | 2 | 5 | 10 | 16 | 31 | 47 | 63 | 76 | 86 | 91 | 0.989 | Gradual disintegration-type |
| | Neutral Solution | 1 | 2 | 6 | 12 | 19 | 34 | 50 | 67 | 81 | 92 | 100 | 0.995 | |
| 27 | Acidic Solution | 1 | 2 | 4 | 8 | 13 | 24 | 38 | 54 | 70 | 82 | 89 | 0.988 | Gradual disintegration-type |
| | Neutral Solution | 2 | 4 | 8 | 12 | 18 | 30 | 45 | 61 | 77 | 92 | 103 | 0.990 | |
| 28 | Acidic Solution | 0 | 1 | 4 | 8 | 14 | 25 | 37 | 48 | 57 | 67 | 76 | 0.997 | Gradual disintegration-type |
| | Neutral Solution | 1 | 2 | 6 | 12 | 18 | 34 | 50 | 67 | 83 | 91 | 100 | 0.991 | |
| 29 | Acidic Solution | 1 | 2 | 6 | 13 | 22 | 41 | 59 | 74 | 83 | 89 | 92 | 0.970 | Gradual disintegration-type |
| | Neutral Solution | 1 | 2 | 8 | 17 | 28 | 50 | 74 | 89 | 96 | | | 0.985 | |
| 30 | Acidic Solution | 1 | 1 | 4 | 9 | 15 | 28 | 41 | 52 | 61 | 70 | 78 | 0.994 | Gradual disintegration-type |
| | Neutral Solution | 1 | 2 | 6 | 13 | 21 | 38 | 57 | 75 | 92 | 97 | | 0.990 | |

TABLE 6

| Ex. | | Dissolution Rate (%) (Upper Column: Acidic Solution, Lower Column: Neutral Solution) | | | | | | | | | | | Correlation coefficient of fixed release rate | Releasing mechanism (Change in shape) |
|---|---|---|---|---|---|---|---|---|---|---|---|---|---|---|
| | | 0.5 h | 1 h | 2 h | 3 h | 4 h | 6 h | 8 h | 10 h | 12 h | 14 h | 16 h | | |
| 31 | Acidic Solution | 7 | 13 | 22 | 31 | 40 | 60 | 80 | 92 | 96 | | | 0.980 | Gradual disintegration-type |
| | Neutral Solution | 6 | 14 | 26 | 40 | 54 | 83 | 99 | | | | | 0.993 | |
| 32 | Acidic Solution | 2 | 5 | 17 | 32 | 47 | 75 | 91 | | | | | 0.992 | Gradual disintegration-type |
| | Neutral Solution | 2 | 5 | 17 | 35 | 56 | 88 | 100 | | | | | 0.978 | |
| Comp. Ex. 1 | Acidic Solution | 1 | 2 | 5 | 7 | 9 | 13 | 18 | 22 | 26 | 30 | 34 | 0.999 | Insoluble matrix-type |
| | Neutral Solution | 1 | 3 | 6 | 9 | 12 | 18 | 23 | 28 | 33 | 37 | 42 | 0.996 | |
| Comp. Ex. 2 | Acidic Solution | 1 | 3 | 7 | 11 | 15 | 22 | 28 | 34 | 38 | 41 | 44 | 0.976 | Hydrogel-type |
| | Neutral Solution | 0 | 1 | 3 | 6 | 9 | 18 | 33 | 56 | 75 | 87 | 93 | 0.969 | |
| Comp. Ex. 3 | Acidic Solution | 31 | 65 | 90 | 96 | | | | | | | | 0.843 | Internal disintegration-type |
| | Neutral Solution | 38 | 75 | 94 | | | | | | | | | 0.867 | |
| Comp. Ex. 4 | Acidic Solution | 1 | 4 | 9 | 14 | 18 | 26 | 33 | 40 | 47 | 56 | 64 | 0.998 | Hydrogel-type |
| | Neutral Solution | 3 | 12 | 34 | 52 | 67 | 94 | | | | | | 0.989 | |
| Comp. Ex. 5 | Acidic Solution | 5 | 14 | 35 | 59 | 77 | 93 | 96 | | | | | 0.893 | Disintegration-type (Vertical breaking-type) |
| | Neutral Solution | 7 | 24 | 66 | 91 | 96 | | | | | | | 0.931 | |

(2) Pharmacologically Active Substance Release Behavior

When all the differences in the dissolution rates between that obtained in the acidic solution and that in the neutral solution at each sampling point fell within 15%, it was determined that the release behavior of the pharmacologically active substance in an acidic pH and that in a neutral pH were similar. This criterion is based on the Guideline for the Design and Evaluation of Controlled-Release Dosage Forms (Oral Dosage Forms), Pharmacy and Therapeutics Committee, No. 1, Vol. 5, issued on Mar. 11, 1988, which states that the acceptable range for setting the dissolution is ±10-15%.

Table 7 shows the results.

TABLE 7

| Example | Maximum value of the difference in dissolution rates |
| --- | --- |
| 6 | 10% |
| 7 | 10% |
| 8 | 10% |
| 9 | 10% |
| 10 | 6% |
| 11 | 6% |
| 12 | 8% |
| 13 | 5% |
| 14 | 3% |
| 15 | 5% |
| 16 | 4% |
| 17 | 10% |
| 18 | 3% |
| 19 | 9% |
| 20 | 10% |
| 23 | 10% |
| 24 | 9% |
| 25 | 8% |
| 26 | 9% |
| 27 | 14% |
| 29 | 15% |
| 32 | 13% |

From Table 7, it was confirmed that the pharmacologically active substance-release behaviors of the preparation produced in these Examples were similar in the acidic solution and in the neutral solution.

Test Example 3

Pharmacokinetic Study Using Beagle Dogs

Using the tablets produced in Example 22, the Pharmacokinetic Study was conducted.

The tablets produced in Example 22 (containing 60 mg of tolvaptan) were placed in gelatin capsules for dogs, and 3 to 5 beagles were orally administered one of the thus-obtained gelatin capsules either postprandially or under fasting (one capsule per dog). Blood samples were collected with time to measure the concentrations of tolvaptan in the blood. In the same manner, a tablet containing 60 mg of tolvaptan (an immediate-release preparation that comprises amorphous tolvaptan together with hydroxypropylcellulose, lactose, cornstarch, crystalline cellulose, hydroxypropylcellulose, low substituted hydroxypropylcellulose and magnesium stearate) was orally administered as a Comparative Example under fasting. Blood samples were collected with time to measure the concentrations of tolvaptan in the blood.

Table 8 shows the pharmacokinetic parameters obtained by the above-mentioned oral administration test.

TABLE 8

| Administered preparation | AUCt (ng · hr/ml) | AUCinf (ng · hr/ml) | Cmax (ng/ml) | Tmax (hr) | MRTt (hr) |
| --- | --- | --- | --- | --- | --- |
| Example 22 | | | | | |
| Administration under fasting | 602 ± 80 | 771 ± 32 | 189 ± 25 | 5.3 ± 1.2 | 5.42 ± 0.46 |
| Postprandial administration | 857 ± 403 | 1139 ± 619 | 234 ± 97 | 4.4 ± 1.7 | 4.90 ± 0.96 |
| Comparative Example | | | | | |
| Tablets Administration under fasting | 1058 ± 630 | 1234 ± 769 | 322 ± 132 | 2.0 ± 1.0 | 3.42 ± 0.60 |

In Table 8, AUCt indicates the area under the blood concentration-time curve (trapezoidal rule), AUCinf indicates the area under the blood concentration-time curve up to infinite time, Cmax indicates the maximum drug concentration, Tmax indicates the time to reach the maximum drug concentration, and MRTt indicates the mean residence time.

As is clear from Table 8, the preparation produced in Example 22 was designed to release the pharmacologically active substance over about 6 hours. The change in the concentration of the pharmacologically active substance in the blood after the gavage administration was similar to that of the pharmacologically active substance-release behavior. Specifically, in the preparation of Example 22 that was designed to release the pharmacologically active substance over 6 hours, the concentration of the pharmacologically active substance reached the maximum at about 6 hours from the administration. In particular, when the preparation of Example 22 was administered under fasting, the variance (standard error) of the concentration of the pharmacologically active substance in blood between individuals was very small compared with that of the immediate-release preparation (Comparative Example). This indicates that the sustained-release preparation of the present invention will not be greatly influenced by the variance between individuals.

When the preparation of Example 22 was administered postprandially, the concentration of the pharmacologically active substance in the blood reached the maximum 4 to 6 hours after the administration. The postprandial concentration of the pharmacologically active substance in the blood tends to become slightly high; however, the concentration of the pharmacologically active substance in the blood as an overall was not greatly changed by having a meal. It can thus be concluded that the preparation of the present invention is a sustained-release preparation that is little affected by having a meal.

The invention claimed is:

1. A gradual disintegration-type and matrix-type pharmaceutical solid preparation comprising:
   (a) tolvaptan;
   (b) calcium polycarbophil; and
   (c) a sugar and/or sugar alcohol, the (c) sugar and/or sugar alcohol being at least one member selected from the group consisting of trehalose, lactitol, maltose, maltitol, sucrose, sorbitol, xylitol, erythritol, mannitol, lactose, and isomaltooligosaccharide.

2. The pharmaceutical solid preparation according to claim 1, wherein the amount of the (b) calcium polycarbophil is 1 to 50 wt. %.

3. The pharmaceutical solid preparation according to claim 1, wherein the amount of the (c) sugar and/or sugar alcohol is 0.1 to 70 wt. %.

4. The pharmaceutical solid preparation according to claim 1, further comprising (d) water-insoluble fine particles.

5. The pharmaceutical solid preparation according to claim 4, wherein the (d) water-insoluble fine particles are particles that can reduce pores in the preparation.

6. The pharmaceutical solid preparation according to claim 4, wherein the average particle diameter of the (d) water-insoluble fine particles is 0.002 to 50 µm.

7. The pharmaceutical solid preparation according to claim 1, further comprising (e) a wicking-type disintegrant.

8. The pharmaceutical solid preparation according to claim 7, wherein the (e) wicking-type disintegrant is carmellose.

9. The pharmaceutical solid preparation according to claim 4, wherein the (d) water-insoluble fine particles are at least one member selected from the group consisting of colloidal silicon dioxide, hydrated silicon dioxide, light anhydrous silicic acid, talc, titanium oxide, magnesium stearate, and ethyl cellulose.

10. The pharmaceutical solid preparation according to claim 9, wherein the average particle diameter of the (d) water-insoluble fine particles is 0.002 to 50 µm.

11. The pharmaceutical solid preparation according to claim 4, wherein the amount of the (d) water-insoluble fine particles is 0.01 to 30 wt. %.

12. The pharmaceutical solid preparation according to claim 7 wherein the amount of the (e) wicking-type disintegrant is 0.1 to 15 wt. %.

13. The pharmaceutical solid preparation according to claim 1, wherein the (c) sugar and/or sugar alcohol is at least one member selected from the group consisting of trehalose, lactitol, maltose, maltitol, sucrose, sorbitol, xylitol, and isomaltooligosaccharide.

14. The pharmaceutical solid preparation according to claim 1, wherein the (c) sugar and/or sugar alcohol is at least one member selected from the group consisting of maltose monohydrate, maltitol, lactitol monohydrate, and trehalose dihydrate.

15. The pharmaceutical solid preparation according to claim 1, wherein the amount of the (a) tolvaptan is 0.01 to 80 wt. %.

16. The pharmaceutical solid preparation according to claim 4, further comprising (e) a wicking-type disintegrant.

17. The pharmaceutical solid preparation according to claim 16, wherein the (e) wicking-type disintegrant is carmellose.

18. The pharmaceutical solid preparation according to claim 1, wherein the solid preparation is an oral formulation.

* * * * *